US009458194B2

(12) United States Patent
Ferrer Montiel et al.

(10) Patent No.: US 9,458,194 B2
(45) Date of Patent: Oct. 4, 2016

(54) COMPOUNDS USEFUL IN THE TREATMENT AND/OR CARE OF THE SKIN AND THEIR COSMETIC OR PHARMACEUTICAL COMPOSITIONS

(71) Applicant: Lubrizol Advanced Materials, Inc., Cleveland, OH (US)

(72) Inventors: Antonio Vicente Ferrer Montiel, Alicante (ES); Núria Almiñana Doménech, Barcelona (ES); Juan Cebrián Puche, Barcelona (ES); Wim Van Den Nest, Vilanova i la Geltru (ES); Cristina Carreño Serraïma, Barcelona (ES); Raquel Delgado González, Gavá (ES)

(73) Assignee: Lubrizol Advanced Materials, Inc., Wickliffe, OH (US)

( * ) Notice: Subject to any disclaimer, the term of this patent is extended or adjusted under 35 U.S.C. 154(b) by 0 days.

(21) Appl. No.: 14/783,689

(22) PCT Filed: Apr. 15, 2014

(86) PCT No.: PCT/EP2014/057672
§ 371 (c)(1),
(2) Date: Oct. 9, 2015

(87) PCT Pub. No.: WO2014/170347
PCT Pub. Date: Oct. 23, 2014

(65) Prior Publication Data
US 2016/0075738 A1 Mar. 17, 2016

(30) Foreign Application Priority Data
Apr. 15, 2013 (EP) ..................... 13382138

(51) Int. Cl.
| | | |
|---|---|---|
| A61K 38/00 | (2006.01) | |
| A61K 38/39 | (2006.01) | |
| A61K 47/48 | (2006.01) | |
| A61P 17/00 | (2006.01) | |
| A61P 35/00 | (2006.01) | |
| A61P 9/10 | (2006.01) | |
| A61P 27/02 | (2006.01) | |
| A61K 38/06 | (2006.01) | |
| A61K 38/07 | (2006.01) | |
| A61K 38/08 | (2006.01) | |
| A61K 38/04 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 5/113 | (2006.01) | |
| C07K 5/02 | (2006.01) | |
| C07K 5/083 | (2006.01) | |
| C07K 5/09 | (2006.01) | |
| C07K 5/093 | (2006.01) | |
| A61K 8/64 | (2006.01) | |
| A61Q 19/08 | (2006.01) | |
| A61K 8/04 | (2006.01) | |
| A61K 8/06 | (2006.01) | |
| A61K 8/14 | (2006.01) | |
| A61K 9/127 | (2006.01) | |

(Continued)

(52) U.S. Cl.
CPC ............. *C07K 5/1021* (2013.01); *A61K 8/044* (2013.01); *A61K 8/068* (2013.01); *A61K 8/14* (2013.01); *A61K 8/64* (2013.01); *A61K 9/127* (2013.01); *A61K 38/07* (2013.01); *A61K 38/08* (2013.01); *A61K 45/06* (2013.01); *A61Q 19/08* (2013.01); *C07K 5/0215* (2013.01); *C07K 5/0806* (2013.01); *C07K 5/0815* (2013.01); *C07K 5/0819* (2013.01); *C07K 7/06* (2013.01); *A61K 38/00* (2013.01)

(58) Field of Classification Search
None
See application file for complete search history.

(56) References Cited

U.S. PATENT DOCUMENTS 8,404,231 B2 * 3/2013 Li ..................... A01K 67/0276
424/70.1
2004/0126788 A1 * 7/2004 Schiemann ...... G01N 33/57484
435/6.14

(Continued)

OTHER PUBLICATIONS

Anonymous "Technical Report: UPLEVITY". Published Jun. 2013.*

(Continued)

*Primary Examiner* — Christina Bradley
*Assistant Examiner* — Zachary J Miknis
(74) *Attorney, Agent, or Firm* — Fay Sharpe LLP

(57) ABSTRACT

Compounds of general formula (I): their stereoisomers, mixtures thereof and/or their cosmetically or pharmaceutically acceptable salts, cosmetic and/or pharmaceutical compositions which contain them and their use in medicine, and in the treatment and/or care of the skin, particularly in the aging and photoaging of the skin, and more particularly for the treatment and/or prevention of wrinkles and/or stretch marks.

$$R_1-AA_1-AA_2-NH-\underset{\underset{NHR_3}{\overset{\overset{O}{\parallel}}{\underset{(CH_2)_n}{\overset{|}{CH}}}}}{C}-AA_3-R_2 \quad (I)$$

20 Claims, No Drawings

(51) Int. Cl.
A61K 45/06 (2006.01)
C07K 7/06 (2006.01)

(56) References Cited

U.S. PATENT DOCUMENTS

2005/0188427 A1* 8/2005 Li ............... A01K 67/0276
800/8
2008/0227692 A1* 9/2008 Flugelman ............ A61K 38/39
514/1.1

OTHER PUBLICATIONS

Anonymous. "The Heart and Vascular Disease" http://www.webmd.com/heart-disease/vascular-disease?page=3. Published Nov. 10, 2010.*
Albericio, F., et al., "Preparation and application of the 5-(4-(9-fluorenylmethyloxycarbonyl) aminomethyl-3,5-dimethoxyphenoxy)valeric acid (PAL) handle for the solid phase synthesis of C-terminal peptide amides under mild conditions," J. Org. Chem., vol. 55, pp. 3730-3743 (1990).
Atherton, E., et al., "Solid Phase Peptide Synthesis: A practical approach," IRL Oxford University Press. pp. 1-61 (1989).
Barlos K. et al., "Darstellung geschützter Peptid-Fragmente unter Einsatz substituierter Triphenylmethyl-Harze," Tetrahedron Lett., vol. 30, pp. 3943-3946 (1989). English Abstract only.
Barlos K. et al., "Veresterung von partiell geschützten Peptid-Fragmenten mit Harzen. Einsatz von 2-Chlortritylchlorid zur Synthese von Leu$^{15}$Gastrin I," Tetrahedron Lett., vol. 30, pp. 3947-3951(1989). English Abstract only.
Bellingham, C.M., et al., "Self-aggregation of recombinantly expressed human elastin polypeptides," Biochim. Biophys. Acta, vol. 1550, pp. 6-19 (2001).
Berge, S.M., et al., "Pharmaceutical Salts," J. Pharm. Sci., vol. 66 (1), pp. 1-19 (1977).
Bodanzsky, M., et al., "The practice of peptide synthesis," $2^{nd}$. Edn., pp. 75-126, Springer-Verlag (1994).
Borel, A., et al., "Lysyl oxidase-like protein from bovine aorta," J. Biol. Chem., vol. 276 (52), pp. 48944-48949 (2001).
Brown-Augsburger, P., et al., "Identification of an elastin cross-linking domain that joins three peptide chains," J. Biol. Chem., vol. 270 (3), pp. 17778-17783 (1995).
Cenizo, V., et al., "LOXL as a target to increase the elastin content in adult skin: a dill extract induces the LOXL gene expression" vol. 15, pp. 574-581 (2006).
Choi, J., et al., "Analysis of dermal elastic fibers in the absence of fibulin-5 reveals potential roles for fibulin-5 in elastic fiber assembly," Matrix Biol., vol. 28(4), pp. 211-220 (2009).
Christensen, T., "A quantitative test for monitoring coupling completeness in solid phase peptide synthesis using chloranil," Acta Chem. Scand. vol. 33B, pp. 763-766 (1979).
Csiszar, K., "Lysyl oxidases: a novel multifunctional amine oxidase family," Prog. Nucleic Acid Res. Mol. Biol., vol. 70, pp. 1-32 (2001).
CTFA International Cosmetic Ingredient Dictionary & Handbook, 12th Edition, pp. 3040-3065 (2008).
Debelle, L., et al., "Elastin: molecular description and function," Int. J. Biochem. & Cell Biol., vol. 31, pp. 261-272 (1999).
Elsner, P., Antimicrobials and the skin physiological and pathological flora, "in Hipler, U.-C., et al., Biofunctional Textiles and the Skin," Curr. Probl. Dermatol., vol. 33, pp. 35-41 (2006).

Faury, G., "Function-structure relationship of elastic arteries in evolution: from microfibrils to elastin and elastic fibres," Pathol. Biol. (Paris), vol. 49, pp. 310-325 (2001).
Gacko, M., "Elastin: structure, properties and metabolism," Cellular & Molecular Biology Letters, vol. 5, pp. 327-348 (2000).
Hermida, N., et al., "A synthetic peptide from transforming growth factor-$\beta_1$ type III receptor prevents myocardial fibrosis in spontaneously hypertensive rats," Cardiovascular Research, vol. 81, No. 3, pp. 601-609 (2008).
Hirai, M., et al., "Fibulin-5/DANCE has an elastogenic organizer activity that is abrogated by proteolytic cleavage in vivo," J. Cell. Biol., vol. 176 (7), pp. 1061-1071 (2007).
IUPAC-IUB Commission of Biochemical Nomenclature specified in Eur. J. Biochem., vol. 138, pp. 9-37 (1984).
Kaiser, E., et al., "Color test for detection of free terminal amino groups in the solid-phase synthesis of peptides," Anal. Biochem., vol. 34(2), pp. 595-598 (1970).
Kullmann, W., "Proteases as catalysts for enzymic syntheses of opioid peptides," J. Biol. Chem., vol. 255(17), pp. 8234-8238 (1980).
Lloyd-Williams, P., et al., "Chemical Approaches to the Synthesis of Peptides and Proteins," CRC Press, Synthesis in solution, enzymatic synthesis, pp. 19-93 (1997).
Lloyd-Williams, P., et al., "Convergent Solid-Phase Peptide Synthesis," Tetrahedron, vol. 49(48), pp. 11065-11133 (1993).
Malcolm, R.K., et al., "Controlled release of a model antibacterial drug from a novel self-lubricating silicone biomaterial," J. Cont. Release, vol. 97(2), pp. 313-320 (2004).
Matsueda, G.R., et al., "A p-methylbenzhydrylamine resin for improved solid phase synthesis of peptide amides," Peptides, vol. 2, 45-50 (1981).
Nelson, "Application of microencapsulation in textiles," Int. J. Pharm., vol. 242(1-2), pp. 55-62 (2002).
Rink, H., "Solid phase synthesis of protected peptide fragments using a trialkoxy-diphenyl-methylester resin," Tetrahedron Lett., vol. 28 (33), pp. 3787-3790 (1987).
Roberts, D.C., et al., "Unusual amino acids in peptide synthesis," in The Peptides, vol. 5, Chapter 6, Gross and Meienhofer, J., Eds., Academic Press, New York, pp. 341-449 (1983).
Santiago, B., et al., "Topical application of a peptide inhibitor of transforming growth factor-$\beta$1 ameliorates bleomycin-induced skin fibrosis," J. Investigative Dermatology, Nature Publishing Group, GB, vol. 125, No. 3, pp. 450-455 (Sep. 2005).
Schaab, Impregnating Fabrics with Microcapsules, HAPPI, pp. 84-86 (1986).
Stewart, J.M., et al., "Solid-phase Peptide Synthesis," $2^{nd}$ Edition, pp. 1-20 (1984).
Tassabehji, M., et al., "An elastin gene mutation producing abnormal tropoelastin and abnormal elastic fibres in a patient with autosomal dominant cutis laxa," Hum. Mol. Genet., vol. 7(6), pp. 1021-1028 (1998).
Wang, S.-S., "p-Alkoxybenzyl Alcohol Resin and p-Alkoxybenzyloxycarbonylhydrazide Resin for Solid Phase Synthesis of Protected Peptide Fragments," J. Am. Chem. Soc., vol. 95(4), pp. 1328-1333 (1973).
Watson, R.E.B., et al., "Fibrillin-rich microfibrils are reduced in photoaged skin. Distribution at the dermal-epidermal junction," J. Invest. Dermatol., vol. 112 (5), pp. 782-787 (1999).
Wilkinson, J.B., et al., "Harry's Cosmeticology," Seventh edition, pp. 50-73 and 728-787 (1982).
Zheng, et al., "Molecular Analysis of Fibulin-5 function during de novo synthesis of elastic fibers," Mol. Cell. Biol., vol. 27, pp. 31083-1095 (2007).

* cited by examiner

SEQUENCE LISTING

<160> NUMBER OF SEQ ID NOS: 45

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Asp Val Lys Tyr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Glu Val Lys Tyr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Asn Val Lys Tyr
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Gln Val Lys Tyr
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Asp Ile Lys Tyr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Asp Leu Lys Tyr
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Asp Met Lys Tyr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Orn

<400> SEQUENCE: 8

Asp Val Xaa Tyr
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Dpr

<400> SEQUENCE: 9

Asp Val Xaa Tyr
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Dbu

<400> SEQUENCE: 10

Asp Val Xaa Tyr
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 11

Asp Val Lys Trp
1

```
<210> SEQ ID NO 12
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 12

Glu Val Lys Trp
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 13

Asp Ile Lys Trp
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Orn

<400> SEQUENCE: 14

Asp Val Xaa Trp
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 15

Asn Ile Lys Tyr
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 16

Asn Leu Lys Tyr
1

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Dpr
```

<400> SEQUENCE: 17

Asn Val Xaa Tyr
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 18

Gln Ile Lys Tyr
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide

<400> SEQUENCE: 19

Gln Leu Lys Tyr
1

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide

<400> SEQUENCE: 20

Gln Met Lys Tyr
1

<210> SEQ ID NO 21
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Dbu

<400> SEQUENCE: 21

Gln Val Xaa Tyr
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 22

Gln Val Lys Trp
1

<210> SEQ ID NO 23
<211> LENGTH: 4
<212> TYPE: PRT

```
<213> ORGANISM: Artificial Sequence
<220> FEATURE:
<223> OTHER INFORMATION: Synthetic Peptide

<400> SEQUENCE: 23

Glu Ile Lys Trp
1

<210> SEQ ID NO 24
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Orn

<400> SEQUENCE: 24

Glu Leu Xaa Tyr
1

<210> SEQ ID NO 25
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Dpr

<400> SEQUENCE: 25

Asn Ile Xaa Tyr
1

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Dbu

<400> SEQUENCE: 26

Gln Val Xaa Trp
1

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Orn

<400> SEQUENCE: 27

Gln Ile Xaa Tyr
1

<210> SEQ ID NO 28
```

```
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is Orn

<400> SEQUENCE: 28

Glu Leu Xaa Trp
1

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 29

Asp Val Lys Tyr
1

<210> SEQ ID NO 30
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 30

Asp Val Lys Tyr
1

<210> SEQ ID NO 31
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 31

Glu Val Lys Tyr
1

<210> SEQ ID NO 32
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
```

```
<222> LOCATION: (1)..(1)
<223> OTHER INFORMATION: ACETYLATION

<400> SEQUENCE: 32

Gln Val Lys Tyr
1

<210> SEQ ID NO 33
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 33

Asp Leu Lys Tyr
1

<210> SEQ ID NO 34
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 34

Asp Met Lys Tyr
1

<210> SEQ ID NO 35
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is Orn

<400> SEQUENCE: 35

Asp Val Xaa Tyr
1

<210> SEQ ID NO 36
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is Dbu
```

```
<400> SEQUENCE: 36

Asp Val Xaa Tyr
1

<210> SEQ ID NO 37
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 37

Glu Val Lys Trp
1

<210> SEQ ID NO 38
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 38

Asn Ile Lys Tyr
1

<210> SEQ ID NO 39
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is Dpr

<400> SEQUENCE: 39

Asn Val Xaa Tyr
1

<210> SEQ ID NO 40
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 40

Gln Met Lys Tyr
1

<210> SEQ ID NO 41
```

```
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Orn

<400> SEQUENCE: 41

Gln Val Xaa Tyr
1

<210> SEQ ID NO 42
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 42

Gln Val Lys Trp
1

<210> SEQ ID NO 43
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is Dpr

<400> SEQUENCE: 43

Asn Ile Xaa Tyr
1

<210> SEQ ID NO 44
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is Dbu
<220> FEATURE:
<221> NAME/KEY: MOD_RES
<222> LOCATION: (4)..(4)
<223> OTHER INFORMATION: AMIDATION

<400> SEQUENCE: 44
```

```
Gln Val Xaa Trp
1

<210> SEQ ID NO 45
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Orn

<400> SEQUENCE: 45

Asn Ile Xaa Trp
1
```

COMPOUNDS USEFUL IN THE TREATMENT AND/OR CARE OF THE SKIN AND THEIR COSMETIC OR PHARMACEUTICAL COMPOSITIONS

This application claims the benefit of PCT/EP2014/057672, filed Apr. 15, 2014, and EP 13382138.9, filed Apr. 15, 2013, from which the PCT application claims priority, the disclosures of which are incorporated herein by reference in their entireties.

FIELD OF THE INVENTION

This invention relates to compounds capable of increasing the firmness of the skin and it refers to cosmetic or pharmaceutical compositions which contain said compounds that are useful in the treatment and/or care of the skin, preferably for the treatment and/or care of those conditions, disorders and/or diseases that improve with the stimulation of LOXL1 or fibulin-5 synthesis.

INTRODUCTION

The skin is formed by three layers: stratum corneum, dermis and epidermis. The stratum corneum is the outermost layer of the epidermis and it is the layer which is in direct contact with the environment. It is formed by flattened, dead cells called corneocytes and it is the skin's first protective barrier. The epidermis is composed of keratinocytes, melanocytes and Langerhans cells. The main cell population in the epidermis is keratinocytes, which form a keratinized layer that continually renews itself. Their function is to protect against external agents, whether these be physical, chemical or pathogens. The dermis is located deeper in the skin and is joined to the epidermis by means of the basal membrane. It is formed by fibroblasts, adipocytes and macrophages; it is irrigated by blood vessels and presents numerous nerve endings responsible for transmitting sensations of touch and temperature. Hair follicles as well as sweat, sebaceous and apocrine glands are located in the dermis, and their function is to maintain the integrity and elasticity of the skin. These properties are provided by its extracellular matrix, comprised of proteins secreted by fibroblasts.

The proteins of the extracellular matrix (ECM) are classified in two groups: glycosaminoglycans and scleroproteins. Glycosaminoglycans (GAGs) are unbranched chains resulting from the polymerization of amino-sugar disaccharides. Due to their chemical properties and their large number of negative charges, GAGs form very voluminous structures and tend to capture large quantities of water, enabling the ECM to be resistant to compression. Scleroproteins have structural and adhesive functions, and the two main ones are: elastin and collagen, which are responsible for the mechanical properties of the tissues, such as the ability to resist tension, compression, extensibility and torsion. The elasticity and resilience properties of ECM are due to a network of elastic fibers.

Elastic fibers are important for the maintenance of the skin's elasticity, but also in other tissues and organs, such as lungs or large blood vessel walls [Faury G., "*Function-structure relationship of elastic arteries in evolution: from microfibrils to elastin and elastic fibres*", Pathol. Biol. (Paris), (2001), 49, 310-325]. Defects in the formation of elastic fibers, such as mutations in the genes which codify the different proteins that comprise them, give rise to different pathologies. Thus, mutations in the gene fibrillin-1 cause the appearance of Marfan syndrome (associated with skeletal, ocular and cardiovascular symptoms); mutations in the gene fibrillin-2 give rise to congenital contractural arachnodactyly, as well as ocular and skeletal symptoms, and mutations in the elastin gene cause Williams syndrome, supravalvular stenosis and cutis laxa [Tassabehji M. et al., "*An elastin gene mutation producing abnormal tropoelastin and abnormal elastic fibres in a patient with autosomal dominant cutis laxa*", Hum. Mol. Genet., (1998), 6, 1021-1028].

The objective of elastic fibers is to maintain elasticity during the individual's entire life. However, there are enzymes which are capable of degrading them giving rise to a loss of the skin's elasticity, which is a factor that notably contributes to the aging of connective tissues and have an important role in the skin's degeneration due to exposure to the sun [Watson R. E. B. et al., "*Fibrillin-rich microfibrils are reduced in photoaged skin. Distribution at the dermal-epidermal junction*", J. Invest. Dermatol., 1999, 112, 782-787].

Structurally, elastic fibers are comprised of a nucleus of elastin covered by a sheath of microfibrils of approximately 10 nm in diameter. The microfibrils are formed by fibrillin and glycoprotein associated with microfibrils (MAGP). The assembly of the elastic fibers is sequential, the microfibrils appearing first and forming a frame upon which the elastin is deposited. Elastin is a highly hydrophobic protein, comprised by approximately 750 amino acidic residues and comes from a hydrosoluble initiator, tropoelastin, which is secreted into the extracellular space by the fibroblasts. Elastin fibers are the result of the assembly and crosslinking of tropoelastin monomers near the plasma membrane of the fibroblasts.

Pretropoelastin is the initiating molecule of tropoelastin. It is synthesized in the ribosomes of the rough endoplasmic reticulum of the fibroblasts, cells of the smooth muscle, endothelial cells, macrophages, chondroblasts and leucocytes. It is formed by 747 amino acids, of which the first 26 N-terminal amino acids are a peptide signal which, when cut, turn pretropoelastin into tropoelastin [Gacko M., "*Elastin: structure, properties and metabolism*", Cellular & Molecular Biology Letters, (2000) 5, 327-348]. The tropoelastin molecule is soluble, has a molecular weight of almost 70 kDa, and presents hydrophobic domains alternated with crosslinking domains in its sequence [Brown-Augsburger P. et al., "*Identification of an elastin crosslinking domain that joins three peptide chains*", J. Biol. Chem., (1995), 270, 17778-17783]. Hydrophobic domains are repetitions of peptides with two to nine amino acids rich in proline, alanine, valine, leucine, isoleucine and glycine, with valine and glycine being particularly abundant [Debelle L. et al., "*Elastin: molecular description and function*", Int. J. Biochem. Cell Biol., (1999), 31, 261-272]. Interactions between hydrophobic domains are important in the assembly and are essential for the elasticity of the molecule [Bellingham C. M. et al., "*Self-aggregation of recombinantly expressed human elastin polypeptides*", Biochim. Biophys. Acta, (2001), 1550, 6-19]. The crosslinking domains of tropoelastin contain lysine residues in regions rich in proline or polyalanine regions. The formation of desmosine covalent crosslinking due to the action of lysyl oxidases stabilizes the polymerized, soluble product [Csiszar K., "*Lysyl oxidases: a novel multifunctional amine oxidase family*", Prog. Nucleic Acid Res. Mol. Biol., (2001), 70, 1-32] and only two lysyl oxidase proteins, called LOX and LOXL, are able to crosslink insoluble elastin [Borel A. et al., "*Lysyl oxidase-like protein from bovine aorta*", J. Biol. Chem., (2001),276, 48944-48949]. In addition, the sequence of the translated tropoelastin has a negatively charged hydrophilic C-terminal domain which is highly conserved between species. The principal post-translational modifications suffered by this molecule are hydroxylations of proline residues.

Elastogenesis is the process which leads to the generation of functional elastin in elastic fibers. It begins inside the cell with the synthesis of the tropoelastin molecule, to which a galactolectin of 67 kDa is bound which acts as a chaperone preventing the tropoelastin molecules being aggregated intracellularly. The complex is secreted into the extracellular space where the galactolectin interacts with the microfibril galactosugars, thus reducing its affinity to tropoelastin, which is locally released. Galactolectin of 67 kDa is recycled and can carry out its function again, whilst tropoelastin is deposited in the frame formed by the microfibrillar components by means of the interaction of the N-terminal domain of the glycoprotein associated with microfibrils (MAGP) with the C-terminal domain of tropoelastin. Tropoelastin, in turn, interacts with the protein fibulin-5 (also called DANCE or EVEC), which acts as a nucleus to which tropoelastin adheres. Firstly, fibulin-5 adheres to the integrins of the cell surface through its N-terminal fragment (although this step is not crucial) and to the microfibrils through the protein fibrillin-1, the major component of the microfibrils. Tropoelastin is then bound to fibulin-5 and the microfibrils through a coacervation process, forming a fibrillin-1/fibulin-5/tropoelastin complex.

Once the tropoelastin molecules are aligned a crosslinking occurs between the lysines of different tropoelastin molecules to form the insoluble elastin polymer. This process is carried out by Lysyl Oxidase (LOX) and Lysyl Oxidase-like (LOXL). The majority of tropoelastin lysine residues are deaminated and oxidized to their aldehyde form due to the action of LOX dependent on $Cu^{2+}$, forming a desmosine nucleus. The crosslinking occurs due to the reaction of said aldehyde forms between themselves or with an unmodified lysine, and as a consequence of this the tropoelastin chains become insoluble and the elastin network grows. Mature elastin is an insoluble polymer of tropoelastins covalently bound by crosslinking, which can be bi-, tri- or tetrafunctional. The increase in the complexity is believed to progress over time. The hydrophobic fragments demonstrate great mobility and largely contribute to the entropy of the system, to which the quantity of water that hydrates the polymer in vivo also contributes [Debelle L. et al., "*Elastin: molecular description and function*", Int. J. Biochem. Cell. Biol., (1999), 31, 261-272].

Fibulins are a family of proteins of between 50 and 200 kDa formed by seven proteins from the extracellular matrix characterized by having tandem arrays of a variety of epidermal growth factors (EGF-like) dependent on calcium and a fragment characteristic of C-terminal fibulin. They can be classified as Class I, which includes the longer fibulins, (fibulin-1, fibulin-2 and fibulin-6) and Class II, which includes the shorter ones (fibulin-3, fibulin-5, fibulin-5 and fibulin-7). Within the fibulin family we can highlight fibulin-5, which is directly involved in the elastogenesis process [Zheng et al., "*Molecular Analysis of Fibulin-5 function during de novo synthesis of elastic fibers*", Mol. Cell. Biol., (2007), 27, 31083-1095]. Fibulin-5 contains an RGD fragment genetically conserved which recognizes integrin receptors and helps it to participate in cell processes. Fibulin-5 has affinity for tropoelastin, but not for polymerized elastin, which suggests its role in the first steps of elastogenesis. It has also been noticed that fibulin-5 accelerates the coacervation process of tropoelastin [Hirai M. et al., "*Fibulin-5/DANCE has an elastogenic organizer activity that is abrogated by proteolytic cleavage in vivo*", J. Cell. Biol., (2007), 176, 1061-1071]. This coacervation process is favored by the temperature and high concentrations of sodium chloride. Furthermore, fibulin-5 limits the maturation of coacervated elastin. This data is consistent with that observed in the bibliography [Choi et al., "*Analysis of dermal elastic fibers in the absence of fibulin-5 reveals potential roles for fibulin-5 in elastic fiber assembly*", Matrix Biol., (2009), 28, 211-220], in which knockout rats for fibulin-5 had much thicker fragments of elastin than normal rats. Fibulin-5 also interacts with crosslinking enzymes such as LOXL. It has been witnessed that rats deficient in fibulin-5 show premature aging characteristics which include sagging of the skin, emphysema and seized arteries. It has also been verified that the levels of fibulin-5 decrease with age, making the skin increasingly less elastic and firm [Hirai M. et al., "*Fibulin-5/DANCE has an elastogenic organizer activity that is abrogated by proteolytic cleavage in vivo*", J. Cell. Biol., (2007), 176,1061-1071].

Lysyl Oxidase (LOX) is a family of extracellular proteins dependent on copper that catalyzes the formation of aldehydes using the lysines present in elastin and collagen. These aldehydes that are formed are very reactive and react with each other producing a crosslinking of molecules which is vital for the stabilization of the elastin and collagen fibers. There are five members in the family, a LOX and four counterparts of lysyl oxidase (LOX-like, LOXL), LOXL1 to LOXL4. Each of the proteins contains an N-terminal peptide signal, a variable central region and a C-terminal region that shows similarities in the sequence. Of the five members of the LOX family it has been observed that those which are directly involved in the elastogenesis process are LOX and LOXL1. It has been observed that with age LOX and LOXL decrease, therefore the elastogenesis process becomes less efficient [Cenizo V. et al., "*LOXL as a target to increase the elastin content in adult skin: a dill extract induces the LOXL gene expression*", (2006), 15,574-581].

The patent application US 2005/188427 describes the increase of LOXL1 for the treatment of wrinkles, saggy skin, treatment of chronic obstructive pulmonary disease (COPD), for example and not restricted to, emphysema, asthma or chronic bronchitis, treatment of the degradation of the elastic lamina of the Brunch membrane, treatment of age-related macular degeneration, treatment of pelvic organ prolapse or urinary incontinence.

The patent application US 2004/126788 describes the increase of fibulin-5 for the reduction of tumorigenicity and angiogenesis.

The patent application US2008/227692 describes the increase of fibulin-5 for the treatment of diabetic retinopathy and age-related macular degeneration.

BRIEF DESCRIPTION

Thus, this invention provides a solution to the existing needs and comprises new peptide sequences capable of stimulating the synthesis of lysyl oxidase-like-1 and/or fibulin-5 and which are characterized in that the following monomeric unity is found in position three of the peptide sequence:

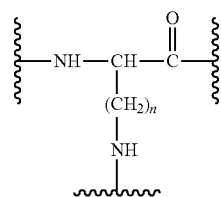

with n equal to 1, 2, 3 or 4.

In one aspect, the invention relates to a compound of general formula (I):

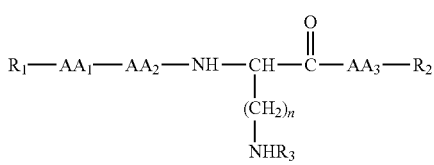

its stereoisomers, mixtures thereof and/or its cosmetic or pharmaceutical acceptable salts, wherein $AA_1$ is selected from the group consisting of -Asp-, -Glu-, -Asn-, -Gln-, -Lys- and -Gly-;

$AA_2$ is selected from the group consisting of -Val-, -Leu-, -Ile-, -Met-, -Cit-, -His-, -Thr- and -Gln-;

$AA_3$ is selected from the group consisting of -Tyr-, -Trp- and 4-Abz;

n is selected from the group consisting of 1, 2, 3 and 4.

$R_3$ is selected from the group consisting of H, or -$AA_2$-$AA_1$-$R_1$.

$R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_6$—CO—, wherein $R_6$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —$NR_4R_5$, —$OR_4$ and —$SR_4$, wherein $R_4$ and $R_5$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ or $R_2$ are not α-amino acids with the condition that if $R_3$ is H, then $AA_2$ is selected from the group consisting of -Val-, -Leu-, -Ile- and -Met-, and $AA_1$ is selected from the group consisting of -Asp-, -Glu-, -Asn- and -Gln-.

DESCRIPTION OF THE INVENTION

Definitions

In order to facilitate the comprehension of this invention, the meanings of some terms and expressions as they are used in the context of the invention are included.

In the context of this invention "skin" is understood as the layers which comprise it, from the uppermost layer or stratum corneum to the lowermost layer or hypodermis, both inclusive. These layers are composed of different types of cells such as keratinocytes, fibroblasts, melanocytes, mastocytes, neurons and/or adipocytes, among others. The term "skin" also comprises the scalp.

The term "treatment", as used in the context of this specification when it is not accompanied by the qualifications "cosmetic, non-therapeutic", means the administration of a compound according to the invention to alleviate or eliminate a disease or disorder or reduce or eliminate one or more symptoms associated with this disease or disorder. The term "treatment" also covers the ability to alleviate or eliminate the physiological consequences of the disease or disorder.

When the term "treatment" is accompanied by the qualifications "cosmetic, non-therapeutic" they refer to the application of the compound to the skin, hair and/or mucous membranes in particular with the aim of improving the cosmetic qualities of the skin, hair and/or mucous membranes such as and not restricted to, their level of hydration, elasticity, firmness, shine, tone or texture, among others. The term "care" in this invention refers to the maintenance of the qualities of the skin, hair and/or mucous membranes. These qualities are subject to improvement and maintained through a cosmetic treatment and/or care of the skin, hair and/or mucous membranes both in healthy subjects as well as those which present diseases and/or disorders of the skin and/or mucous membranes, such as and not restricted to, ulcers and lesions on the skin, psoriasis, dermatitis, acne or rosacea, among others.

The term "prevention", as used in this invention, refers to the ability of a compound of the invention to prevent, delay or hinder the appearance or development of a disease or disorder before its appearance.

In the context of this invention, the term "aging" refers to the changes experienced by the skin with age (chronoaging) or through exposure to the sun (photoaging) or to extreme environmental climatic conditions of cold or wind, chemical contaminants or pollutants, and includes all the external visible and/or perceptible changes through touch, such as and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of several environmental factors such as exposure to tobacco smoke, exposure to pollution, and climatic conditions such as cold and/or wind also contributes to the aging of the skin.

In this description the abbreviations used for amino acids follow the recommendations of the 1983 IUPAC-IUB Commission of Biochemical Nomenclature specified in *Eur. J. Biochem.*, (1984), 138, 937.

Thus, for example, Gly represents $NH_2-CH_2-COOH$, Gly- represents $NH_2-CH_2-CO-$, -Gly represents $-NH-CH_2-COOH$ and -Gly- represents $-NH-CH_2-CO-$. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

Structures of the amino acid residues and their nomenclature in one and three letter code

| Name | Residue | Symbol | Residue |
|---|---|---|---|
| Asparagyl -Asn- N | | Glutaminyl -Gln- Q | |
| Histidyl -His- H | | Glycyl -Gly- G | |
| Lysyl -Lys- K | | Tyrosyl -Tyr- Y | |
| Leucyl -Leu- L | | Aspartyl -Asp- D | |
| Glutamyl -Glu- E | | Isoleucyl -Ile- I | |

TABLE 1-continued

Structures of the amino acid residues and their nomenclature in one and three letter code

| Name | Residue | Symbol | Residue |
|---|---|---|---|
| Valyl -Val- V | | Methionyl -Met- M | |
| Tryptophyl -Trp- W | | Ornithyl -Orn- | |
| Diaminobutyryl -Dbu- | | Diaminopropionyl -Dpr- | |
| 4-Aminobenzoyl -4-Abz- | | Citrullyl -Cit- | |
| Threonyl -Thr- | | | |

The abbreviation "Ac-" is used in this description to designate the acetyl group ($CH_3$—CO—), the abbreviation "Palm-" is used to designate the palmitoyl group ($CH_3$—$(CH_2)_{14}$—CO—) and the abbreviation "Myr-" is used to designate the myristoyl group ($CH_3$—$(CH_2)_{12}$—CO—).

The term "non-cyclic aliphatic group" is used in this invention to cover alkyl, alkenyl and alkynyl groups, linear or branched.

The term "alkyl group" refers to a linear or branched saturated group which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a simple bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a group, linear or branched, which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a simple bond, including, for example and not restricted to, the vinyl group (—$CH_2$=$CH_2$), allyl (—$CH_2$—CH=$CH_2$), oleyl, linoleyl and similar.

The term "alkynyl group" refers to a group, linear or branched, which has between 2 and 24, preferably between 2 and 16, more preferably between 2 and 14, even more preferably between 2 and 12, yet more preferably 2, 3, 4, 5 or 6 carbon atoms, with one or more triple carbon-carbon bonds, preferably 1, 2 or 3 triple carbon-carbon bonds, conjugated or unconjugated, which is bound to the rest of the molecule by a simple bond, including, for example and not restricted to, the ethynyl group, 1-propynyl, 2-propynyl, 1-butynyl, 2-butynyl, 3-butynyl, pentynyl, such as 1-pentynyl, and similar. The alkynyl groups can also contain one or more double carbon-carbon bonds, including for example and not restricted to, the group but-1-en-3-ynyl, pent-4-en-1-ynyl and similar.

The term "alicyclic group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and is bound to the rest of the molecule by a simple bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, bound to the rest of the molecule by a simple bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, bound to the rest of the molecule by a simple bond, including, for example and not restricted to, the cyclooct-2-in-1-yl group and similar. The cycloalkynyl groups can also contain one or more double carbon-carbon bonds, including for example and not restricted to, the cyclooct-4-en-2-ynyl group and similar.

The term "aryl group" refers to an aromatic group which has between 6 and 30, preferably between 6 and 18, more preferably between 6 and 10, even more preferably between 6 or 10 carbon atoms, which comprises 1, 2, 3 or 4 aromatic rings, bound by a carbon-carbon bond or condensed, including, for example and not restricted to, phenyl, naphthyl, diphenyl, indenyl, phenanthryl or anthranyl, among others; or an aralkyl group.

The term "aralkyl group" refers to an alkyl group substituted by an aromatic group, with between 7 and 24 carbon atoms and including, for example and not restricted to, —(CH$_2$)$_{1-6}$-phenyl, —(CH$_2$)$_{1-6}$-(1-naphthyl), —(CH$_2$)$_{1-6}$-(2-naphthyl), —(CH$_2$)$_{1-6}$—CH(phenyl)$_2$ and similar.

The term "heterocyclyl group" refers to a hydrocarbonated ring of 3-10 members, in which one or more of the atoms in the ring, preferably 1, 2 or 3 of the atoms in the ring, is a different element to carbon, such as nitrogen, oxygen or sulfur and can be saturated or unsaturated. For the purposes of this invention, the heterocycle can be a monocyclic, bicyclic or tricyclic system, which can include systems of condensed rings; and the nitrogen, carbon or sulfur atoms can optionally be oxidized in the radical heterocycle; the nitrogen atom can optionally be quaternized; and the radical heterocyclyl can be partially or completely saturated or aromatic. The greatest preference is for the term heterocyclyl to refer to a ring of 5 or 6 members. Examples of saturated heterocyclic groups are dioxane, piperidine, piperazine, pyrrolidine, morpholine and thiomorpholine. Examples of aromatic heterocyclic groups, also known as heteroaromatic groups are pyridine, pyrrole, furan, thiophene, benzofuran, imidazoline, quinolein, quinoline, pyridazine and naphthyridine.

The term "heteroarylalkyl group" refers to an alkyl group substituted by a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example and not restricted to, —(CH$_2$)$_{1-6}$-imidazolyl, —(CH$_2$)$_{1-6}$-triazolyl, —(CH$_2$)$_{1-6}$-thienyl, —(CH$_2$)$_{1-6}$-furyl, —(CH$_2$)$_{1-6}$-pyrrolidinyl and similar.

As is understood in this technical field, there can be a certain level of substitution of the aforementioned groups. Therefore, there can be substitution in any of the groups of this invention where specifically stated. The references in this document to substituted groups in the groups of this invention indicate that the specified radical can be substituted in one or more positions available by one or more substituents, preferably in 1, 2 or 3 positions, more preferably in 1 or 2 positions, yet more preferably in 1 position. These substituents include, C$_1$-C$_4$ alkyl; hydroxyl; C$_1$-C$_4$ alcoxyl; amino; C$_1$-C$_4$ aminoalkyl; C$_1$-C$_4$ carbonyloxyl; C$_1$-C$_4$ oxycarbonyl; halogen such as fluoride, chlorine, bromine and iodine; cyano; nitro; azide; C$_1$-C$_4$ alkylsulfonyl; thiol; C$_1$-C$_4$ alkylthio; aryloxyl such as phenoxyl; —NR$_b$ (C=NR$_b$)NR$_b$R$_c$; wherein R$_b$ and R$_c$ are independently selected from the group formed by H, C$_1$-C$_4$ alkyl, C$_2$-C$_4$ alkenyl, C$_2$-C$_4$ alkynyl, C$_3$-C$_{10}$ cycloalkyl, C$_6$-C$_{18}$ aryl, C$_7$-C$_{17}$ aralkyl, heterocyclyl of 3-10 members or protective group of the amino group.

Compounds of the Invention

The applicant of this invention has found a solution for the aforementioned problem regarding stimulation of synthesis of LOXL-1 and/or fibulin-5. A first aspect of the invention refers to a compound of general formula (I):

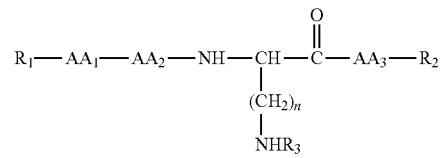

its stereoisomers, mixtures thereof and/or its cosmetically or pharmaceutically acceptable salts, where AA$_1$ is selected from the group formed by -Asp-, -Glu-, -Asn-, -Gln-, -Lys- and -Gly-, AA$_2$ is selected from the group formed by -Val-, -Leu-, -Ile-, -Met-, -Cit-, -His-, -Thr- and -Gln-;

AA$_3$ is selected from the group formed by -Tyr-, -Trp- and 4-Abz;

n is selected from the group formed by 1, 2, 3 and 4.

R$_3$ is selected from the group formed by H, or -AA$_2$-AA$_1$-R$_1$.

R$_1$ is selected from the group formed by H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_6$—CO—, wherein $R_6$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group formed by —$NR_4R_5$, —$OR_4$ and —$SR_4$, wherein $R_4$ and $R_5$ are independently selected from the group formed by H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ or $R_2$ are not α-amino acids.

with the condition that if $R_3$ is H, then $AA_2$ is selected from the group formed by -Val-, -Leu-, -Ile- and -Met-, and $AA_1$ is selected from the group formed by -Asp-, -Glu-, -Asn- and -Gln-.

In accordance with a preferred embodiment, $R_1$ is selected from the group formed by H, a polymer derived from polyethylene glycol and $R_6$—CO—, wherein $R_6$ is selected from the group formed by substituted or unsubstituted alkyl radical $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain of 1 to 6 carbon atoms and $R_6$—CO— is not an α-amino acid. More preferably, $R_1$ is selected from the group formed by H, a polymer derived from polyethylene glycol with a molecular weight comprised between 200 and 35000 Daltons, acetyl, tert-butanoyl, prenyl, hexanoyl, 2-methylhexanoyl, cyclohexanecarboxyl, octanoyl, decanoyl, lauroyl myristoyl, palmitoyl, stearoyl, oleoyl and linoleoyl. Even more preferably, $R_1$ is H, acetyl, lauroyl, myristoyl or palmitoyl. In an even more preferred embodiment, $R_1$ is acetyl or palmitoyl.

In accordance with another preferred embodiment, $R_2$ is selected from the group formed by —$NR_4R_5$, —$OR_4$, —$SR_4$, wherein $R_4$ and $R_5$ are independently selected from the group formed by H, a polymer derived from polyethylene glycol, substituted or unsubstituted $C_1$-$C_{24}$ alkyl, substituted or unsubstituted alkenyl $C_2$-$C_{24}$, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted cycloalkynyl $C_8$-$C_{24}$, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and —$NR_4R_5$ is not an α-amino acid. Optionally, $R_4$ and $R_5$ can be bound by a saturated or unsaturated carbon-carbon bond, forming a cycle with the nitrogen atom. More preferably $R_2$ is —$NR_4R_5$ or —$OR_4$. More preferably, $R_4$ and $R_5$ are independently selected from the group formed by H, a polymer derived from polyethylene glycol with a molecular weight comprised between 200 and 35000 Daltons, methyl, ethyl, hexyl, dodecyl and hexadecyl. Even more preferably $R_4$ is H and $R_5$ is selected from the group formed by H, methyl, ethyl, hexyl, dodecyl and hexadecyl. In accordance with an even more preferred embodiment, $R_2$ is selected from —OH and —$NH_2$.

In accordance with another embodiment of this invention $R_1$ is selected from the group formed by H, acetyl, lauroyl, myristoyl and palmitoyl, preferably $R_1$ is selected from the group formed by H, acetyl and palmitoyl and $R_2$ is selected from the group formed by —OH and —$NH_2$.

In accordance with another particular embodiment the most preferred structures of the polymer derived from polyethylene glycol are the group (—$CH_2$—$CH_2$—O)$_r$—H in which r is a number comprised between 4 and 795 and the group

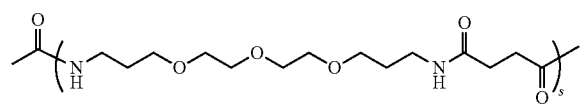

where s is a number comprised between 1 and 125.

In accordance with a preferred embodiment of this invention, $AA_1$ is selected from the group formed by -Asp-, -Glu-, -Asn- and -Gln-, $AA_2$ is selected from the group formed by -Val-, -Leu-, -Ile- and -Met-, $R_3$ is H, $AA_3$ is -Tyr- or -Trp-.

In accordance with a preferred embodiment of this invention, $AA_1$ is selected from the group formed by -Lys-, -Gly- and -Asn-, $AA_2$ is selected from the group formed by -His-, -Thr-, -Gln- and -Cit-, $R_3$ is -$AA_2$-$AA_1$-$R_1$ and $AA_3$ is 4-Abz.

In accordance with another embodiment of this invention $R_1$ is selected from the group formed by H, acetyl, lauroyl, myristoyl and palmitoyl, $AA_1$ is -L-Asp-, $AA_2$ is -L-Val- and $AA_3$ is -L-Tyr-, $R_3$ is H, n is 4, and $R_2$ is selected from the group formed by —$NR_4R_5$ and —$OR_4$ wherein $R_4$ and $R_5$ are independently selected from H, methyl, ethyl, hexyl, dodecyl and hexadecyl. More preferably, $R_1$ is acetyl or palmitoyl and $R_2$ is —$NH_2$.

In accordance with another embodiment of this invention $R_1$ is selected from the group formed by H, acetyl, lauroyl, myristoyl and palmitoyl, $AA_1$ is -L-Lys-, $AA_2$ is -L-His-, $AA_3$ is -4-Abz-, $R_3$ is -$AA_2$-$AA_1$-$R_1$, n is 4 and $R_2$ is selected from the group formed by —$NR_4R_5$ and —$OR_4$ wherein $R_4$ and $R_5$ are independently selected from H, methyl, ethyl, hexyl, dodecyl and hexadecyl. More preferably, $R_1$ is acetyl or palmitoyl and $R_2$ is —$NH_2$.

In accordance with another embodiment of this invention $R_1$ is selected from the group formed by H, acetyl, lauroyl, myristoyl and palmitoyl, $AA_1$ is -L-Asn-, $AA_2$ is -L-Thr-, $AA_3$ is -4-Abz-, $R_3$ is -$AA_2$-$AA_1$-$R_1$, n is 4 and $R_2$ is selected from the group formed by —$NR_4R_5$ and —$OR_4$ wherein $R_4$ and $R_5$ are independently selected from H, methyl, ethyl, hexyl, dodecyl and hexadecyl. More preferably, $R_1$ is acetyl or palmitoyl and $R_2$ is —$NH_2$.

In accordance with another embodiment of this invention $R_1$ is selected from the group formed by H, acetyl, lauroyl, myristoyl and palmitoyl, $AA_1$ is -L-Lys-, $AA_2$ is -L-Thr-, $AA_3$ is -4-Abz-, $R_3$ is -$AA_2$-$AA_1$-$R_1$ and n is 4, $R_2$ is selected from the group formed by —$NR_4R_5$ and —$OR_4$ wherein $R_4$ and $R_5$ are independently selected from H, methyl, ethyl, hexyl, dodecyl and hexadecyl. More preferably, $R_1$ is acetyl or palmitoyl and $R_2$ is —$NH_2$.

In accordance with another embodiment of this invention $R_1$ is selected from the group formed by H, acetyl, lauroyl, myristoyl and palmitoyl, $AA_1$ is -L-Lys-, $AA_2$ is -L-Cit-, $AA_3$ is -4-Abz-, $R_3$ is -$AA_2$-$AA_1$-$R_1$, and n is 4, $R_2$ is selected from the group formed by —$NR_4R_5$ and —$OR_4$ wherein $R_4$ and $R_5$ are independently selected from H, methyl, ethyl, hexyl, dodecyl and hexadecyl. More preferably, $R_1$ is acetyl or palmitoyl and $R_2$ is —$NH_2$.

In accordance with another embodiment of this invention $R_1$ is selected from the group formed by H, acetyl, lauroyl, myristoyl and palmitoyl, $AA_1$ is -L-Gly-, $AA_2$ is -L-Gln-, $AA_3$ is -4-Abz-, $R_3$ is -$AA_2$-$AA_1$-$R_1$ and n is 4, $R_2$ is selected from the group formed by —$NR_4R_5$ and —$OR_4$ wherein $R_4$ and $R_5$ are independently selected from H, methyl, ethyl, hexyl, dodecyl and hexadecyl. More preferably, $R_1$ is acetyl or palmitoyl and $R_2$ is —$NH_2$.

Specifically, compounds which stimulate the synthesis of LOXL-1 and/or fibulin, according to formula (I) include those represented by a peptide sequence selected from the group of peptide sequences outlined in Table 2, in which their sequence identifier is detailed, wherein, optionally, the N-terminal amino acid of the peptide sequence is modified to include a group corresponding to $R_1$ in formula (I) and, optionally, the C-terminal amino acid of the peptide sequence is modified to include a group corresponding to $R_2$ in formula (I):

TABLE 2

| SEQUENCE | IDENTIFIER |
|---|---|
| Asp-Val-Lys-Tyr | SEQ ID NO. 1 |
| Glu-Val-Lys-Tyr | SEQ ID NO. 2 |
| Asn-Val-Lys-Tyr | SEQ ID NO. 3 |
| Gln-Val-Lys-Tyr | SEQ ID NO. 4 |
| Asp-Ile-Lys-Tyr | SEQ ID NO. 5 |
| Asp-Leu-Lys-Tyr | SEQ ID NO. 6 |
| Asp-Met-Lys-Tyr | SEQ ID NO. 7 |
| Asp-Val-Orn-Tyr | SEQ ID NO. 8 |
| Asp-Val-Dpr-Tyr | SEQ ID NO. 9 |
| Asp-Val-Dbu-Tyr | SEQ ID NO. 10 |
| Asp-Val-Lys-Trp | SEQ ID NO. 11 |
| Glu-Val-Lys-Trp | SEQ ID NO. 12 |
| Asp-Ile-Lys-Trp | SEQ ID NO. 13 |
| Asp-Val-Orn-Trp | SEQ ID NO. 14 |
| Asn-Ile-Lys-Tyr | SEQ ID NO. 15 |
| Asn-Leu-Lys-Tyr | SEQ ID NO. 16 |
| Asn-Val-Dpr-Tyr | SEQ ID NO. 17 |
| Gln-Ile-Lys-Tyr | SEQ ID NO. 18 |
| Gln-Leu-Lys-Tyr | SEQ ID NO. 19 |
| Gln-Met-Lys-Tyr | SEQ ID NO. 20 |
| Gln-Val-Dbu-Tyr | SEQ ID NO. 21 |
| Gln-Val-Lys-Trp | SEQ ID NO. 22 |

TABLE 2-continued

| SEQUENCE | IDENTIFIER |
|---|---|
| Glu-Ile-Lys-Trp | SEQ ID NO. 23 |
| Glu-Leu-Orn-Tyr | SEQ ID NO. 24 |
| Asn-Ile-Dpr-Tyr | SEQ ID NO. 25 |
| Gln-Val-Dbu-Trp | SEQ ID NO. 26 |
| Gln-Ile-Orn-Tyr | SEQ ID NO. 27 |
| Glu-Leu-Orn-Trp | SEQ ID NO. 28 |
| Lys-His-Lys-(Lys-His)-4-Abz | |
| Asn-Thr-Lys-(Asn-Thr)-4-Abz | |
| Lys-Thr-Lys-(Lys-Thr)-4-Abz | |
| Lys-Cit-Lys-(Lys-Cit)-4-Abz | |
| Gly-Gln-Lys-(Gly-Gln)-4-Abz | | their stereoisomers, mixtures thereof, and/or their cosmetically or pharmaceutically acceptable salts.

In this invention the branched sequences are represented in a linear form as they are at the right in the following table.

TABLE 3

| | |
|---|---|
| Lys-His-Lys-4Abz<br>   |<br>  His<br>   |<br>  Lys | Lys-His-Lys(Lys-His)-4-Abz |
| Asn-Thr-Lys-4Abz<br>   |<br>  Thr<br>   |<br>  Asn | Asn-Thr-Lys(Asn-Thr)-4-Abz |
| Lys-Thr-Lys-4Abz<br>   |<br>  Thr<br>   |<br>  Lys | Lys-Thr-Lys(Lys-Thr)-4-Abz |
| Lys-Cit-Lys-4Abz<br>   |<br>  Cit<br>   |<br>  Lys | Lys-Cit-Lys(Lys-Cit)-4-Abz |
| Gly-Gln-Lys-4Abz<br>   |<br>  Gln<br>   |<br>  Gly | Gly-Gln-Lys(Gly-Gln)-4-Abz |

The compounds of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., enantiomers or diastereomers.

For example, when it is stated that $AA_1$ can be -Lys-, it is understood that $AA_1$ is selected from -L-Lys-, -D-Lys- or mixtures of both, racemic or non-racemic. The preparation procedures described in this document enable the person skilled in the art to obtain each of the stereoisomers of the compound of the invention by choosing the amino acid with the right configuration.

In the context of this invention, the term "amino acids" includes the amino acids encoded by the genetic code as well as non-encoded amino acids, whether they are natural or not. Examples of non-encoded amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4 diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, α-amino acids and β-amino acids, among others, as well as their derivatives. A list of non-natural amino acids can be found in the article "*Unusual amino acids in peptide synthesis*" by D. C. Roberts and F. Vellaccio, in *The Peptides,* Vol. 5 (1983), Chapter VI, Gross E. and Meienhofer J., Eds., Academic Press, New York, USA or in the commercial catalogs of the companies specialized in the field.

The cosmetically and pharmaceutically acceptable salts of the peptides provided by this invention are also found within the field of this invention. The term "cosmetically or pharmaceutically acceptable salts" means a salt recognized for its use in animals and more specifically in human beings, and includes salts used to form base addition salts, either they are inorganic, such as and not restricted to, lithium, sodium, potassium, calcium, magnesium, manganese, copper, zinc or aluminum among others, either they are organic, such as and not restricted to, ethylamine, diethylamine, ethylenediamine, ethanolamine, diethanolamine, arginine, lysine, histidine or piperazine among others, or acid addition salts, either they are organic, such as and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, such as and not restricted to, chloride, sulfate, borate or carbonate, among others. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al., "*Pharmaceutical Salts*", (1977), *J. Pharm. Sci.,* 66, 119].

Preparation Procedures of the Compounds of the Invention

Synthesis of the compounds of the invention, their stereoisomers, mixtures thereof and/or their cosmetically or pharmaceutically acceptable salts can be carried out according to conventional methods, known in the prior art, such as using solid phase peptide synthesis methods [Stewart J. M. and Young J. D., "*Solid Phase Peptide Synthesis, 2nd edition*", (1984), Pierce Chemical Company, Rockford, Ill.; Bodanszky M. and Bodanszky A., "*The practice of Peptide Synthesis*", (1994), Springer Verlag, Berlin; Lloyd-Williams P. et al., "*Chemical Approaches to the Synthesis of Peptides and Proteins*", (1997), CRC, Boca Raton, Fla., USA], synthesis in solution, enzymatic synthesis [Kullmann W. "*Proteases as catalysts for enzymic syntheses of opioid peptides*", (1980), *J. Biol. Chem.,* 255(17), 82348238] or any combination thereof. Compounds can also be obtained by fermentation of a strain of bacteria, modified or unmodified, by genetic engineering with the objective of producing the desired sequences, or by controlled hydrolysis of proteins with animal, fungal, or preferably plant origins, which release peptide fragments which contain, at least, the desired sequence.

For example, a method of obtaining the compounds (I) of the invention, their stereoisomers and mixtures thereof comprises the stages of:
  coupling of an amino acid, with the N-terminal end protected and the C-terminal end free, with an amino acid with the N-terminal end free and the C-terminal end protected or bound to a solid support;
  elimination of the group protecting the N-terminal end;
  repetition of the coupling sequence and elimination of the group protecting the N-terminal end until the desired peptide sequence is obtained;
  elimination of the group protecting the C-terminal end or cleavage of the solid support.

Preferably, the C-terminal end is bound to a solid support and the procedure is carried out in solid phase and, therefore, comprises the coupling of an amino acid with the protected N-terminal end and the free C-terminal end with an amino acid with the N-terminal end free and the C-terminal end bound to a polymeric support; elimination of the group protecting the N-terminal end; and repetition of this sequence as many times as is necessary to thus obtain the compound of the desired length, finally followed by the cleavage of the synthesized compound from the original polymeric support.

The functional groups of the side chains of the amino acids are maintained conveniently protected with temporary or permanent protective groups throughout synthesis, and can be unprotected simultaneously or orthogonally to the process of cleavage of the peptide from the polymeric support.

Alternatively, solid phase synthesis can be carried out using a convergent strategy coupling a peptide with the polymeric support or with a peptide or amino acid previously bound to the polymeric support. Convergent synthesis strategies are widely known by persons skilled in the art and are described in Lloyd-Williams P et al., "*Convergent Solid-Phase Peptide Synthesis*", (1993), *Tetrahedron,* 49(48), 11065-11133.

The procedure can comprise the additional stages of deprotection of the N-terminal and C-terminal ends and/or cleavage of the peptide from the polymeric support in an indiscriminate order, using standard procedures and conditions known in the prior art, after which the functional groups of these ends can be modified. The optional modification of the N-terminal and C-terminal ends can be carried out with the peptide of formula (I) anchored to the polymeric support or once the peptide has been separated from the polymeric support.

Optionally, $R_1$ can be introduced by the reaction of the N-terminal end of the compound of the invention with a $R_1$—X compound, wherein $R_1$ has the aforementioned meaning and X is a leaving group, such as and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the compound of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the cleavage process of the peptide from the polymeric support.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl) ethyloxycarbonyl (Teoc), 9-fluorenylmethyloxycarbonyl (Fmoc) or allyloxycarbonyl (Alloc), Trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxocyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (Trt ester), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others; preferred protective groups of the invention are the All, tBu, cHx, Bzl and Trt esters.

The side chains of the trifunctional amino acids can be protected during the synthetic process with temporary or permanent protective groups orthogonal to the protective groups of the N-terminal and C-terminal ends.

The hydroxyl group of the tyrosine side chain can be protected with the group 2-bromobenzyloxycarbonyl (2-BrZ), tBu, All, Bzl or 2,6-dichlorobenzyl (2,6-diClZ) among others. The histidine side chain can be protected with a protective group selected from the group formed by Tos, Dnp, methyl (Me), Boc, benzyloxymethyl (Bom), Bzl, Fmoc, Mts, Trt and Mtt. The amide group of the glutamine and asparagine side chain can be protected by the Trt group or the xanthyl (Xan) group or be used unprotected. For the protection of the carboxyl group of the glutamic acid and aspartic acid side chain esters such as tBu ester, All ester, triphenylmethyl ester (Trt ester), cHx ester, Bzl ester, ortho-nitrobenzyl ester, para-nitrobenzyl ester, para-methoxybenzyl ester, trimethylsilyl ethyl ester, 2-phenylisopropyl ester, Fm ester or Dmab ester, among others, can be used. The indole group of the tryptophan side chain can be protected by the formyl group (For), Boc, Mts or can be used unprotected. For the protection of the amino groups of the lysine, ornithine, diaminobutyric acid and diaminopropionic acid side chains the following groups can be used: amides such as amide acetate, amide benzoate, amide pivalate; carbamates, such as Cbz or Z, ClZ, pNZ, Boc, Troc, Teoc, Fmoc or Alloc, Trt, Mtt, Dnp, Dde, ivDde, Adpoc, among others. The side chain of methionine can be protected by sulfoxide, by sulfone or can be used unprotected. The side chain of threonine can be protected by a protective group selected from the group formed by tBu, Bzl, Trt and Ac.

In a preferred embodiment, the protective group strategy used is the strategy wherein the amino groups are protected by Boc, the carboxyl groups are protected by Bzl, cHx or All esters, the tyrosine side chain is protected by 2-BrZ or Bzl, the histidine side chain is protected by the group Tos or Bom, the glutamic acid and aspartic acid side chain are protected by Bzl, cHx or All, glutamine and asparagine are used unprotected in their side chain, the tryptophan side chain is protected by For or Mts, methionine is used unprotected in its side chain, the lysine, ornithine, diaminobutyric acid and diaminopropionic acid side chains are protected by ClZ, Fmoc, Boc or Alloc, and the threonine side chain is protected by the Bzl group.

In another preferred embodiment, the protective group strategy used is the strategy wherein the amino groups are protected by Fmoc, the carboxyl groups are protected by tBu, All or Trt esters, the tyrosine side chain is protected by tBu, the histidine side chain is protected by the group Trt or Mtt, the glutamic acid and aspartic acid side chain is protected by tBu or All, glutamine and asparagine are used protected by the Trt group in its side chain, the tryptophan side chain is protected by Boc or is used unprotected, methionine is used unprotected in its side chain, the lysine, ornithine, diaminobutyric acid and diaminopropionic acid side chains are protected by Boc, Fmoc, Trt or Alloc, and the threonine side chain is protected by the tBu group.

Examples of these and other additional protective groups, their introduction and removal, can be found in the literature [Atherton B. and Sheppard R. C., "*Solid Phase Peptide Synthesis: A practical approach*", (1989), IRL Oxford University Press]. The term "protective groups" also includes the polymeric supports used in solid phase synthesis.

When synthesis takes place totally or partially in solid phase, the possible solid supports used in the procedure of the invention involve polystyrene supports, polyethylene glycol grafted to polystyrene and similar, such as and not restricted to, p-methylbenzhydrylamine resins (MBHA) [Matsueda G. R. et al., "*A p-methylbenzhydrylamine resin for improved solid phase synthesis of peptide amides*", (1981), *Peptides,* 2, 4550], 2-chlorotrityl resins [Barlos K. et al., "*Darstellung geschützter PeptidFragmente unter Einsatz substituierter TriphenylmethylHarze*", (1989), *Tetrahedron Lett.,* 30, 39433946; Barlos K. et al., "*Veresterung von partiell geschützten PeptidFragmenten mit Harzen. Einsatz von 2-Chlorotritylchlorid zur Synthese von Leu1Gastrin I*", (1989), *Tetrahedron Lett.,* 30, 39473951], TentaGel® resins (Rapp Polymere GmbH), ChemMatrix® resins (Matrix Innovation, Inc.) and similar, which may or may not include a labile linker, such as 5-(4-aminomethyl-3,5-dimethoxyphenoxy) valeric acid (PAL) [Albericio F. et al., "*Preparation and application of the 5-(4-(9-fluorenylmethyloxycarbonyl)aminomethyl-3,5-dimethoxy-phenoxy)valeric acid (PAL) handle for the solid phase synthesis of C-terminal peptide amides under mild conditions*", (1990), *J. Org. Chem.,* 55, 37303743], 2-[4-aminomethyl-(2,4-dimethoxyphenyl)]phenoxyacetic acid (AM) [Rink H., "*Solid phase* synthesis of protected peptide fragments using a trialkoxy-diphenyl-methylester resin", (1987), *Tetrahedron Lett.,* 28, 3787-3790], Wang [Wang S. S., "*p-Alkoxybenzyl Alcohol Resin and p-Alkoxybenzyloxycarbony/hydrazide Resin for Solid Phase Synthesis of Protected Peptide Fragments*", (1973), *J. Am. Chem. Soc.,* 95, 1328-1333] and similar, which enable simultaneous deprotection and cleavage of the peptide from the polymeric support.

Cosmetic or Pharmaceutical Compositions of the Invention

The compounds of the invention can be administered to inhibit neuronal exocytosis by any means which causes contact between the compounds and the site of action in a mammal's body, preferably that of a human being, and in the form of a composition which contains them.

In this regard, another aspect of the invention is a cosmetic or pharmaceutical composition which comprises at least one compound of general formula (I), its stereoisomers, mixtures thereof, and/or its cosmetically or pharmaceutically acceptable salts together with at least one cosmetically or pharmaceutically acceptable adjuvant. These compositions can be prepared by conventional means known to persons skilled in the art ["*Harry's Cosmeticology"*, Seventh edition, (1982), Wilkinson J. B., Moore R. J., ed. Longman House, Essex, GB].

The compounds of this invention have variable solubility in water, according to the nature of their amino acid sequence or any possible modifications in the N-terminal and/or C-terminal ends. Therefore, the compounds of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerin, butylene glycol or polyethylene glycol or any combination thereof.

The cosmetically or pharmaceutically effective amount of the compounds of the invention which should be administered, as well as their dosage, will depend on numerous factors, including age, state of the patient, the nature or severity of the condition, disorder or disease to be treated and/or cared for, the route and frequency of administration and the particular nature of the compounds to be used.

"Cosmetically and pharmaceutically effective amount" is understood to mean a non-toxic but sufficient amount of the compound or compounds of the invention to provide the desired effect. The compounds of the invention are used in the cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight).

The compounds of general formula (I), their stereoisomers, mixtures thereof and/or their cosmetic or pharmaceutically acceptable salts, can also be incorporated into cosmetic or pharmaceutical delivery systems and/or sustained release systems.

The term "delivery systems" relates to a diluent, adjuvant, excipient or carrier with which the compound of the invention is administered. These cosmetic or pharmaceutical carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a long period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the peptides of the invention. The amount of compound contained in the sustained release system will depend, for example, on where the composition is to be administered, the kinetics and duration of the release of the compound of the invention, as well as the nature of the condition, disorder and/or disease to be treated and/or cared for.

The compounds of this invention can also be adsorbed on solid organic polymers or solid mineral supports such as and not restricted to, talc, bentonite, silica, starch or maltodextrin among others.

The compositions that contain the compounds of general formula (I), their stereoisomers, mixtures thereof and/or their cosmetic or pharmaceutically acceptable salts, can also be incorporated into fabrics, non-woven fabrics and medical devices which are in direct contact with the skin, thus releasing the compounds of the invention whether by biodegradation of the binding system to the fabric, non-woven fabric or medical device, or by friction between them and the body, due to bodily moisture, the skin's pH or body temperature. Furthermore, the compounds of the invention can be incorporated into the fabrics and non-woven fabrics used to make garments that are in direct contact with the body. Preferably, the fabrics, non-woven fabrics and medical devices containing the compounds of the invention are used for the treatment of those conditions, disorders and/or diseases which improve or are prevented by the stimulation of the synthesis of LOXL-1 or fibulin-5.

Examples of fabrics, non-woven fabrics, garments, medical devices and means for immobilizing the compounds to them, among which are the delivery systems and/or the sustained release systems described above, can be found in the literature and are known in the prior art [Schaab C. K. (1986) HAPPI May 1986; Nelson G., "*Application of microencapsulation in textiles*", (2002), Int. J. Pharm., 242(1-2), 55-62; "*Biofunctional Textiles and the Skin*" (2006) *Curr. Probl. Dermatol.* v. 33, Hipler U. C. and Elsner P., eds. S. Karger AG, Basel, Switzerland; Malcolm R. K. et al., "*Controlled release of a model antibacterial drug from a novel self-lubricating silicone biomaterial*", (2004), *J. Cont. Release*, 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the compounds of the invention, their stereoisomers, mixtures thereof and/or their cosmetically or pharmaceutically acceptable salts, can be used in different types of compositions of topical or transdermal application which optionally include cosmetically or pharmaceutically acceptable excipients necessary for formulating the desired administration form. A person skilled in the art knows the different excipients which can be used in the cosmetic or pharmaceutical compositions which contain the compounds of the invention.

The compositions of topical or transdermal application can be produced in any solid, liquid or semi-solid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders, among others.

The cosmetic or pharmaceutical compositions of the invention may include agents which increase the percutaneous absorption of the compounds of this invention, such as and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the compound of the invention. The application area will be determined by the nature of the condition, disorder and/or disease to be treated and/or cared for.

Furthermore, the cosmetic compositions containing the compounds of general formula (I), their stereoisomers, mixtures thereof and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, pills, powders, granules, chewing gum, solutions, suspensions, emulsions, syrups, elixirs, polysaccharide films, jellies or gelatins, and any other form known by the person skilled in the art. In a particular embodiment, the compounds of the invention can be incorporated into any form of functional food or fortified food, such as and not restricted to, dietary bars or compact or non-compact powders. These powders can be dissolved in water, soda, dairy products, soy derivatives or can be incorporated into dietary bars. The compounds of this invention can be formulated with common excipients and adjuvants for oral compositions or food supplements, such as and not restricted to, fat components, aqueous components, humectants, preservatives, texturizing agents, flavors, aromas, antioxidants and colorants common in the food industry.

Cosmetic or pharmaceutical compositions containing the compounds of general formula (I), their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal, intravascular injections such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the compounds of the invention can be administered.

Among the cosmetically or pharmaceutically acceptable adjuvants contained in the cosmetic or pharmaceutical compositions described in this invention are additional ingredients commonly used in compositions for the treatment and/or care of the skin, for example and not restricted to, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, AQP-3 modulating agents, aquaporin synthesis-modulating agents, proteins of the aquaporin family, hyaluronic acid synthesis-stimulating agents, glycosaminoglycan synthesis-stimulating agents, fibronectin synthesis-stimulating agents, sirtuin synthesis-stimulating agents, sirtuin-activating agents, heat shock proteins, heat shock protein synthesis-stimulating agents, agents stimulating the synthesis of lipids and components of the stratum corneum, ceramides, fatty acids, agents that inhibit collagen degradation, agents that inhibit matrix metalloproteases, agents that inhibit elastin degradation, agents that inhibit serine proteases such as kallikreins, elastase or cathepsin, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, DNA protecting agents, DNA repair agents, stem cell protecting agents, agents for the treatment and/or care of sensitive skin, agents with firming and/or redensifying and/or restructuring activity, anti-stretch mark agents, agents inhibiting neuronal exocytosis, anticholinergic agents, agents inhibiting muscular contraction, antiaging agents, anti-wrinkle agents, antiperspirant agents, anti-inflammatory agents and/or analgesics, anti-itching agents, calming agents, anesthetic agents, inhibitors of acetylcholine-receptor aggregation, agents inhibiting acetylcholinesterase, dermo-relaxant agents, melanin synthesis inhibiting or stimulating agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, antiglycation agents, detoxifying agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments, colorants, dyes, biopolymers, gelling polymers, thickening agents, surfactants, softening agents, emulsifiers, binding agents, preservatives, agents able to reduce or treat bags under the eyes, exfoliating agents, keratolytic agents, desquamating agents, antimicrobial agents, antifungal agents, fungistatic agents, bactericidal agents, bacteriostatic agents, antihyperkeratosis agents, comedolytic agents, antipsoriatic agents, stabilizers, astringents, agents regulating sebum production, lipolytic agents or agents stimulating lipolysis, adipogenic agents, agents modulating PGC-1α, agents modulating PPARγ, agents which increase or reduce the triglyceride content of adipocytes, anti-cellulite agents, agents inhibiting PAR-2 activity, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents inhibiting vascular permeability, venotonic agents, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor masking antiperspirants, chelating agents, plant extracts, essential oils, marine extracts, agents obtained from a biofermentation process, mineral salts, cell extracts, sunscreens and organic or mineral photoprotective agents active against ultraviolet A and/or B rays and/or infrared A rays, or mixtures thereof, provided that they are physically and chemically compatible with the rest of components in the composition and in particular with the compounds of the invention. Furthermore, the nature of said additional ingredients should not alter in an unacceptable way the benefits of the compounds of this invention. The nature of said additional ingredients can be synthetic or natural, such as plant extracts, or come from a biotechnological procedure.

Additional examples are described in *CTFA International Cosmetic Ingredient Dictionary & Handbook, 12th Edition* (2008).

In a particular embodiment, the anti-wrinkle and/or anti-aging agent is selected, for example and not restricted to, the extracts or hydrolyzed extracts of *Vitis vinifera, Rosa canina, Curcuma Tonga, Theobroma cacao, Ginkgo biloba, Leontopodium alpinum* or *Dunaliella salina* among others, Matrixyl® [INCI: Palmitoyl Pentapeptide-4], Matrixyl® 3000 [INCI: Palmitoyl Tetrapeptide-7, Palmitoyl Oligopeptide], Matrixyl® Synthe'6 [INCI: Glycerin, Water, Hydroxypropyl Cyclodextrin, Palmitoyl Tripeptide-38], Essenskin™ [INCI: calcium hydroxymethionine], Renovage [INCI: Teprenone], Resistem™ [INCI: *Globularia Cordifolia* Ferment], Dermaxyl® [INCI: Palmitoyl Oligopeptide], Calmosensine™ [INCI: Butylene Glycol, Acetyl Dipeptide-1 Cetyl Ester], Volulip™ [INCI: Cetearyl Ethylhexanoate, Sorbitan Isostearate, *Portulaca Pilosa* Extract, Sucrose Cocoate, Palmitoyl Tripeptide-38], Subliskin™ [INCI: *Sinorhizobium meliloti* Ferment, Cetyl Hydroxyethyl Cellulose, Lecithin], Biopeptide CL™ [INCI: Palmitoyl Oligopeptide], Biopeptide EL [INCI: Palmitoyl Oligopeptide], Rigin™ [INCI: Palmitoyl Tetrapeptide-3], Bio-bustyl™ [INCI: Glyceryl Polymethacrylate, Rahnella/Soy Protein Ferment, Palmitoyl Oligopeptide], Dynalift™ [INCI: Sodium Polystyrene Sulfonate, *Sorghum Bicolor* Stalk Juice, Glycerin], Idealift™ [INCI: Acetyl Dipeptide-1 Cetyl Ester], *Siegesbeckia* [INCI: *Siegesbeckia Orientalis* Extract], Ovaliss™ [INCI: Coco-glucoside, Caprylyl Glycol, Alcohol, Glaucine], Juvinity™ [INCI: Geranylgeranylisopropanol] or Resistem™ [INCI proposed: *Globularia Cordifolia* Ferment] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum], Preregen® [INCI: *Glycine soja* (Soybean) Protein, Oxido Reductases], Pepha®-Nutrix [INCI: Natural Nutrition Factors], Pepha®-Tight [INCI: Algae Extract, Pullulan], Pentacare-NA [INCI: Hydrolyzed Wheat Gluten, *Ceratonia Siliqua* Gum], Syn®-Tacks [INCI: Glycerin, Palmitoyl Dipeptide-5 Diaminobutyloyl Hydroxythreonine, Palmitoyl Dipeptide-6 Diaminohydroxybutyrate], BeauActive™ MTP [INCI: Hydrolyzed milk protein], Syn®-TC [INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine], Syn®-Hycan [INCI: Tetradecyl Aminobutyroylvalylaminobutyric Urea Trifluoroacetate], Syn®-Glycan [INCI: Tetradecyl Aminobutyroylvalyl-aminobutyric Urea Trifluoroacetate], Regu®-Age [INCI: Hydrolyzed Rice Bran Protein, Oxido Reductases, *Glycine Soja* Protein], Pepha®-Timp [INCI: Human oligopeptide-20], Colhibin™ [INCI: Hydrolyzed Rice Protein], Elhibin™ [INCI: *Glycine Soja* Protein, Disodium cocoamphodiacetate] or All-Q™ Plus [INCI: Ubiquinone, Tocopheryl Acetate] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9], DN-AGE® LS [INCI: *Cassia alata* leaf Extract], Hyalufix™ GL [INCI: *Alpinia Galanga* Leaf Extract], Neurobiox™ [INCI: *Achillea millefolium* Extract,], Deliner™ [INCI: *Zea Mays* (Corn) Kernel Extract], Lys'lastine™ V [INCI: *Peucedanum Graveolens* (Dill) Extract], Extracellium™ [INCI: Hydrolyzed Potato Protein], Proteasyl® TP LS 8657 [INCI: *Pisum sativum* Extract], Flavagrum™ PEG [INCI: PEG-6 Isostearate, Hesperetin Laurate], Micromerol™ [INCI: *Pyrus malus* Fruit Extract], Heather Extract [INCI: *Calluna vulgaris* Extract], Extracellium [INCI: Hydrolyzed Potato Protein], Marine Filling Spheres [INCI: Pentaerythrityl Tetraisostearate, Silica Dimethyl Silylate, Sodium Chondroitin Sulfate, Atelocollagen], Triactigen™ [INCI: Mannitol, Cyclodextrin, Yeast Extract, Disodium Succinate], Eterniskin™ [INCI: *Grifola Frondosa* Fruiting Body Extract, Maltodextrin], Ascotide™ [INCI: Ascorbyl Phosphate Succinoyl Pentapeptide-12], Hyalurosmooth™ [INCI: *Cassia Angustifolia* Seed Polysaccharide], Indinyl™ [INCI: *Cassia Angustifolia* Seed Polysaccharide], Arganyl™ [INCI: *Argania spinosa* Leaf Extract], Sphingoceryl™ Veg [INCI: Phyto-ceramides], Vit-A-Like™ [INCI: *Vigna aconitifolia* Seed Extract], Peptiskin™ [INCI: Arginine/Lysine polypeptide], Prodejine [INCI: Mannitol, Cyclodextrin, Yeast Extract, Disodium Succinate], Aqu'activ™ [INCI: Behenyl Alcohol, Glyceryl Oleate, Cocamide MIPA, Calcium Citrate], Elestan™ [INCI: Glycerin, Manilkara Leaf Extract], Hibiscin™ HP [INCI: *Hibiscus Esculentus* Seed Extract], Proteasyl® TP LS8657 [INCI: *Pisum Sativum* Extract] or Litchiderm™ [INCI: *Litchi Chinensis* Pericarp Extract] marketed by Laboratoires Sérobiologiques/Cognis/BASF, Algisium C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline® [INCI: Acetyl Hexapeptide-30], Aldenine® [INCI: Hydrolyzed Wheat Protein, Hydrolyzed Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman™ [INCI: Dimethylmethoxy Chromanol], Chromabright® [INCI: Dimethylmethoxy Chromanyl Palmitate], Antarcticine® [INCI: Pseudoalteromonas Ferment Extract], dGlyage® [INCI: Lysine HCl, Lecithin, Tripeptide-9 Citrulline], Vilastene™ [INCI: Lysine HCl, Lecithin, Tripeptide-10 Citrulline], Hyadisine® [INCI: Pseudoalteromonas Ferment Extract], Hyanify™ [INCI: Saccharide Isomerate], Diffuporine® [INCI: Acetyl Hexapeptide-37], Silusyne® [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39], Adifyline® [INCI: Acetyl Hexapeptide-38], Delisens™ [INCI: Acetyl Hexapeptide-46], Telangyn™ [proposed INCI: Acetyl Tetrapeptide-33]. Seacode™ [INCI: Pseudoalteromonas Ferment Extract] or Juvefoxo™ [proposed INCI: Acetyl Hexapeptide-50] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract], Quintescine™ IS [INCI: Dipeptide-4], Peptide Vinci 01 [INCI: Penta-decapeptide-1], Peptide Vinci 02™ [INCI: Hexapeptide-3], Aquarize IS™ [INCI: Hydrolyzed Rice Extract], Lanablue® [INCI: Algae extract], Ederline™ [INCI: *Pyrus Malus* (Apple) Seed Extract], Dynachondrine™ ISR [INCI: Hydrolyzed Soy Protein], Prolixir S20™ [INCI: Dimer Tripeptide-43], Phytocohesine™ PSP [INCI: Sodium Beta-Sitosteryl Sulfate, Beta-Sitosterol], Perenityl™ IS [INCI: *Pyrus Communis* (Pear) Seed Extract], Caspaline 14™ [INCI: Hexapeptide-42], Peptide Q10™ [INCI: Pentapeptide-34 Trifluoroacetate], Survixyl IS™ [INCI: Pentapeptide-31], Chronogen™ [INCI: Tetrapeptide-26] or Telosense™ [proposed INCI: Hydrolyzed Soy Protein, Hydrolyzed Yeast Protein] marketed by Vincience/ISP/Ashland, BONT-L-Peptide [INCI: Palmitoyl Hexapeptide-19], TIMP Peptide [INCI: Acetylhexapeptide-20], ECM Moduline™ [INCI: Palmitoyl Tripeptide-28], Renaissance™ [INCI: Hydrolyzed Wheat Protein, Palmitoyl Decapeptide-21, Decapeptide-22, Oligopeptide-78, Zinc Palmitoyl Nonapeptide-14] marketed by Infinitec Activos, Deepaline™ PVB [INCI: Palmitoyl hydrolyzed Wheat Protein], Sepilift® DPHP [INCI: Dipalmitoyl Hydroxyproline], Survicode™ [INCI: Sodium Cocoyl Alaninate], Aquaxyl™ [INCI: Xylitylglucoside, Anhydroxylitol, Xylitol] or Lipacide PVB [INCI: Palmitoyl hydrolyzed Wheat Protein] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] or Hema'Tîte™ [INCI: Hematite] marketed by Gattefossé, Thalassine™ [INCI: Algae Extract] marketed by Biotechmarine, ChroNOline™ [INCI: Caprooyl Tetrapeptide-3], Exo-H™ [INCI: *Alteromonas* Exopolysaccharide Extract], Exo-T™ [INCI: *Vibrio* Exopolysaccharide Extract], Hydriame® [INCI: Water, Glycosaminoglycans, Sclerotium Gum], MDI Complex® [INCI: Glycosaminoglycans], Adipofill™ [INCI: Ornithine, Phospholipids, Glycolipids] or Thymulen® 4 [INCI: Acetyl Tetrapeptide-2] marketed by Atrium/Unipex Innovations/Lucas Meyer Cosmetics, EquiStat [INCI: *Pyrus malus* Fruit Extract, *Glycine soja* Seed Extract], Juvenesce [INCI: Ethoxydiglycol and Caprylic Triglyceride, Retinol, Ursolic Acid, Phytonadione, Ilomastat], Ursolisome™ [INCI: Lecithin, Ursolic Acid, Atelocollagen, Xanthan Gum, Sodium chondroitin sulfate], Basaline™ [INCI: Hydrolyzed Malt Extract], Phytokine™ [INCI: Hydrolyzed Soy Protein], marketed by Coletica/Engelhard/BASF, Ameliox™ [INCI: Carnosine, Tocopherol, *Silybum marianum* Fruit Extract] or PhytoCellTec™ Malus Domestica [INCI: *Malus domestica* Fruit Cell Culture], Lipobelle Soyaglicone™ [INCI: Soy Isoflavones] or DermCom™ [INCI: *Crocus Chrysanthus* Bulb Extract, *Acacia* Senegal Gum, Aqua/Water] marketed by Mibelle Biochemistry, Bioxilift™ [INCI: *Pimpinella anisum* Extract], Papilactyl D® [*Cyperus Esculentus* Tuber Extract], SMS Anti-Wrinkle® [INCI: *Annona squamosa* Seed Extract], Astressyl® [INCI: *Salix Alba* (Willow) Leaf Extract], Pro-Coll-One+® [INCI: Hydrolyzed Soy Protein], Ridulisse C® [INCI: Soybean], Raffermine® [INCI: Hydrolyzed Soy Flour], Toniskin® [INCI: Yeast Extract] or Coheliss® [INCI: Arabinoxylans purified from Rye Seeds], marketed by Silab, ActiMatrix® [INCI: Peptide based mushroom Extract], Peptamide® 6 [INCI: Hexapeptide-11] marketed by Active Organics/Lubrizol, HPS3® [*Paraffinum Liquidum, Padina Pavonica* Thallus Extract] marketed by Alban Muller, DermaPep® A420 [INCI: Myristoyl Tetrapeptide-6, Glycerin, Butylene Glycol] or DermaPep® A350 [INCI: Myristoyl Tripeptide-31, Butylene Glycol] marketed by DermaPep, Phytosphingosine SLC [INCI: Salicyloyl Phytosphingosine], TEGO® Pep 4-17 [INCI: Tetrapeptide-17], Granactive™ AGE [INCI: Palmitoyl Hexapeptide-14, *Lycium Barbarum* Fruit Extract (Goji Berry)], Sphingokine® NP [INCI: Caprooyl Phytosphigosine], TEGO Pep 4-Even [INCI: Glycerin, Tetrapeptide-30] marketed by Evonik Goldschmidt, Collageneer® [INCI: *Helianthus Ann-*

*uus* Seed Oil, *Lupinus Albus* Extract], Effipulp® [INCI: Hydrolyzed Avocado Protein] or Actimp® 1.9.3 [INCI: Hydrolyzed Lupine Protein] marketed by Expanscience Laboratorie, ECM Protect® [INCI: Tripeptide-2], IP 2000 [INCI: Dextran, Trifluoroacetyl Tripeptide-2] or Glycosann® [INCI: Sodium Chondroitin Sulfate] marketed by IEB, Ronacare® Cyclopeptide-5 [INCI: Ectoin, Cyclopeptide-5] marketed by Merck, Ascotide [INCI: Ascorbyl Phosphate Succinoyl Pentapeptide-12] marketed by Peptron, Homeostatine™ [INCI: *Enteromorpha Compressa, Caesalpinia Spinosa*], Pronalen Firming [INCI: Lady's Thistle Extract, Lady's Mantle Extract, Horsetail Extract, Soy Germ Extract, Wheat Germ Extract, Alfalfa Extract, Radish Extract, Water (Aqua), Butylene Glycol, Decyl Glucoside] and Vitasource™ [INCI: Propanediol, Water, Baicalin] marketed by Provital, Reforcyl® [INCI: Glutamine, Decyl Glucoside, Phenethyl Alcohol, *Cistus Incanus* Flower/Leaf/Stem Extract, *Gynostemma Pentaphyllum* Leaf/Stem Extract], Proteolea® [INCI: Levan, Decyl Glucoside, *Olea Europaea* Leaf Extract, Phenethyl Alcohol, *Zizyphus Jujuba* Seed Extract] or Vitaderm™ [INCI: Hydrolyzed Rice Protein, *Ilex Aquifolium* Extract, Sodium Ursolate, Sodium Oleanolate] marketed by Rahn, Peptiskin® [INCI: Arginine/Lysine polypeptide], Nuteline® C [INCI: Hydrolyzed Hazelnut Protein] or Radicaptol® [INCI: Propylene Glycol, Water, *Passiflora Incarnata* Extract, *Ribes Nigrum* Leaf Extract, *Vitis Vinifera* Leaf Extract] marketed by Solabia, StimulHyal [INCI: Calcium Ketogluconate], Dakaline™ [INCI: *Prunus Amygdalus Dulcis, Anogeissus Leiocarpus* Bark Extract], RenovHyal™ [INCI: Sodium Hyaluronate] or Viapure™ *Boswellia* [INCI: Boswellia Serrata Extract] marketed by Soliance, SymPeptide® 222 [INCI: Myristoyl Pentapeptide-8], SymPeptide® 225 [INCI: Myristoyl Pentapeptide-11], SymPeptide® 239 [INCI: Myristoyl Octapeptide-1], SymPeptide® 230 [INCI: Myristoyl Hexapeptide-4] marketed by Symrise, antagonists of the $Ca^{2+}$ channel, for example and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repairing enzymes, for example and not restricted to, photolyase or T4 endonuclease V, or chloride channel agonists, among others.

In a particular embodiment, agents stimulating the synthesis of dermal or epidermal macromolecules is selected, for example and not restricted to, from the group formed by collagen synthesis-stimulating agents, elastin synthesis-stimulating agents, decorin synthesis-stimulating agents, laminin synthesis-stimulating agents, chaperone synthesis-stimulating agents, sirtuin synthesis-stimulating agents, sirtuin-activating agents, aquaporin synthesis-modulating agents, fibronectin synthesis-stimulating agents, agents that inhibit collagen degradation, agents that inhibit elastin degradation, agents that inhibit serine proteases such as kallikreins, leukocyte elastase or cathepsin G, agents stimulating fibroblast proliferation, agents stimulating adipocyte proliferation, agents stimulating or delaying adipocyte differentiation, for example and not restricted to, extracts of *Centella asiatica, Saccharomyces cerevisiae, Solanum tuberosum, Rosmarinus officinalis, Vaccinium angustifolium,* extract of the algae *Macrocystis pyrifera, Padina pavonica,* extract of the plants soy, malt, flax, sage, red clover, kakkon, lupine, extract of hazelnut, extract of maize, extract of yeast, extract of beech bud, extract of legume seeds, extract of plant hormones such as gibberellins, auxins or cytokines, among others, or extract of Salina zooplankton, the product of fermentation of milk with *Lactobacillus Bulgaricus,* asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: Pseudoalteromonas Ferment Extract], Decorinyl® [INCI: Tripeptide-10 Citrulline], Serilesine® [INCI: Hexapeptide-10], Lipeptide [INCI: Hydrolyzed Vegetable Protein], Aldenine® [INCI: Hydrolyzed Wheat Protein, Hydrolyzed Soy Protein, Tripeptide-1], Relistase® [INCI: Acetylarginyltriptophyl Diphenylglycine], Thermostressine® [INCI: Acetyl Tetrapeptide-22], Peptide AC29 [INCI: Acetyl Tripeptide-30 Citrulline], Diffuporine® [INCI: Acetyl Hexapeptide-37], Silusyne® [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline®[INCI: Acetyl Hexapeptide-38] marketed by Lipotec/Lubrizol, Drieline® PF [INCI: Yeast Betaglucan] marketed by Alban Muller, Phytovityl C® [INCI: Aqua, *Zea Mays* Extract] marketed by Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Vincience/ISP/Ashland, minerals such as calcium, among others, retinoids and their derivatives, isoflavonoids, carotenoids, in particular lycopene, pseudodipeptides, retinoids and their derivatives such as retinol or retinyl palmitate, among others, or heparinoids, among others.

In another particular embodiment, the firming and/or redensifying and/or restructuring agent is selected, for example and not restricted to, the group formed by extracts of *Malpighia punicifolia, Cynara scolymus, Gossypium herbaceum, Aloe Barbadensis, Panicum miliaceum, Morus nigra, Sesamum indicum, Glycine soja, Triticum vulgare,* Pronalen® Firming HSC [INCI: *Triticum Vulgare, Silybum Marianum, Glycine Soy, Equisetum Arvense, Alchemilla Vulgaris, Medicago Sativa, Raphanus Sativus*] or Polyplant® Refirming [INCI: Coneflower, Asiatic Centella, Fucus, Fenugreek] marketed by Provital, Lanablue® [INCI: Sorbitol, Algae Extract] marketed by Atrium Biotechnologies/Unipex Innovations, Pepha®-Nutrix [INCI: Natural Nutrition Factor] marketed by Pentapharm/DSM, plants extracts which contain isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma/Croda, Dermosaccharides® HC [INCI: Glycerin, Water (Aqua), Glycosaminoglycans, Glycogen], Aglycal® [INCI: Mannitol, Cyclodextrin, Glycogen, Arctostaphylos Uva Ursi Leaf Extract], Cytokinol® LS [INCI: Hydrolyzed Casein, Hydrolyzed Yeast Protein, Lysine HCl] or Firmiderm® LS9120 [INCI: *Terminalia Catappa* Leaf Extract, *Sambucus Nigra* Flower Extract, PVP, Tannic Acid] marketed by Laboratoires Serobiologiques/Cognis/BASF, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline™ [INCI: Acetyl Hexapeptide-38] marketed by Lipotec/Lubrizol, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard/BASF, Syn®-Coll [INCI: Palmitoyl Tripeptide-5] marketed by Pentapharm/DSM, Hydriame® [INCI: Water (Aqua), Glycosaminoglycans, Sclerotium Gum] marketed by Atrium Biotechnologies/Unipex Innovations or IP2000 [INCI: Dextran, Trifluoroacetyl Tripeptide-2] marketed by Institut Europeen de Biologie Cellulaire/ Unipex Innovations, among others.

Applications

In another aspect, this invention refers to a compound of general formula (I) as defined hereinabove, its stereoisomers, mixtures thereof and/or its cosmetically or pharmaceutically acceptable salts for its use in medicine, in particular for the treatment and/or prevention of cancer, chronic obstructive pulmonary disease (COPD), urinary incontinence, degradation of the elastic lamina of the Brunch membrane, cutis laxa, vascular diseases and disorders, pelvic organ prolapse, age-related macular degeneration and/or diabetic retinopathy.

In a particular embodiment the treatment of cancer is by reduction of angiogenesis and/or tumorigenicity.

In a particular embodiment chronic obstructive pulmonary disease (COPD) is selected, for example and not restricted to, from the group formed by emphysema, asthma or bronchitis.

In another particular embodiment the vascular disease or disorder is selected, for example and not restricted to, from the group formed by aortic dissection, aneurysms, systolic arterial hypertension, restenosis or stroke.

In another particular embodiment the pelvic organ in pelvic organ prolapse is selected, for example and not restricted to, from the group formed by the bladder, uterus, vagina, rectum, urethra, vaginal wall, paraurethral connective tissue and pubourethral ligaments.

In another aspect, this invention refers to a compound of general formula (I) as defined hereinabove, its stereoisomers, mixtures thereof and/or its cosmetically or pharmaceutically acceptable salts for its use in the treatment of the skin.

In another aspect, this invention refers to the use of a compound of general formula (I) as defined hereinabove, its stereoisomers, mixtures thereof and/or its cosmetically or pharmaceutically acceptable salts for the non-therapeutic cosmetic treatment and/or care of the skin. In particular for the treatment and/or prevention of aging and/or photoaging of the skin, and more in particular for the treatment and/or reduction of wrinkles and/or stretch marks.

In another aspect, this invention refers to the use of a compound of general formula (I) as defined hereinabove, its stereoisomers, mixtures thereof and/or its cosmetically or pharmaceutically acceptable salts to increase the elasticity and/or firmness of the skin.

In another aspect, this invention refers to the use of a compound of general formula (I) as defined hereinabove, its stereoisomers, mixtures thereof and/or its cosmetically or pharmaceutically acceptable salts to stimulate collagen and/or elastin synthesis.

In another aspect, this invention refers to the use of a compound of general formula (I) as defined hereinabove, its stereoisomers, mixtures thereof and/or its cosmetically or pharmaceutically acceptable salts for its use in the stimulation of synthesis of LOXL-1 and/or fibulin-5.

Alternatively, an additional aspect of this invention refers to a method of treatment and/or prevention of cancer, chronic obstructive pulmonary disease (COPD), urinary incontinence, degradation of the elastic lamina of the Brunch membrane, cutis laxa, vascular diseases and disorders, pelvic organ prolapse, age-related macular degeneration and/or diabetic retinopathy which comprises the administration of a pharmaceutically effective quantity of at least one compound of general formula (I), its stereoisomers, mixtures thereof and/or its cosmetically or pharmaceutically acceptable salts.

In a particular embodiment the treatment of cancer is by reduction of angiogenesis and/or tumorigenicity.

In another particular embodiment chronic obstructive pulmonary disease (COPD) is selected, for example and not restricted to, from the group formed by emphysema, asthma or bronchitis.

In another particular embodiment the vascular disease or disorder is selected, for example and not restricted to, from the group formed by aortic dissection, aneurysms, systolic arterial hypertension, restenosis or stroke.

In another particular embodiment the pelvic organ in pelvic organ prolapse is selected, for example and not restricted to, from the group formed by the bladder, uterus, vagina, rectum, urethra, vaginal wall, paraurethral connective tissue and pubourethral ligaments.

In another aspect, this invention refers to a method of treatment and/or care of the skin which comprises the administration of a cosmetically or pharmaceutically effective quantity of at least one compound of general formula (I), its stereoisomers, mixtures thereof and/or its cosmetic or pharmaceutical acceptable salts: in particular for the treatment and/or prevention of aging and/or photoaging of the skin, and more particularly, for the treatment and/or reduction of wrinkles and/or stretch marks.

In another aspect, this invention refers to a method of treatment and/or care to increase the elasticity and/or firmness of the skin which comprises the administration of a cosmetically or pharmaceutically effective quantity of at least one compound of general formula (I), its stereoisomers, mixtures thereof and/or its cosmetically or pharmaceutically acceptable salts.

In another aspect, this invention refers to a method of treatment and/or care to stimulate collagen and/or elastin synthesis which comprises the administration of a cosmetically or pharmaceutically effective quantity of at least one compound of general formula (I), its stereoisomers, mixtures thereof and/or its cosmetically or pharmaceutically acceptable salts.

In another aspect, this invention refers to a method of treatment and/or care to stimulate the synthesis of LOXL-1 and/or fibulin-5 which comprises the administration of a cosmetically or pharmaceutically effective quantity of at least one compound of general formula (I), its stereoisomers, mixtures thereof and/or its cosmetically or pharmaceutically acceptable salts.

In another aspect, the compounds of the invention can be administered by any means that causes contact between the compounds and the site of action in a mammal's body, preferably that of a human being, and more preferably in the form of a composition which contains them. The administration of the compounds of this invention is carried out topically, transdermally, orally or parenterally. In another particular aspect the topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of application can vary greatly, depending on the needs of each subject, with a recommendation of an application range from once a month to 10 times a day, preferably from once a week to 4 times a day, more preferably from three times a week to twice a day, even more preferably once a day.

The following specific examples provided here serve to illustrate the nature of this invention. These examples are included for illustrative purposes and should not be interpreted as limitations to the invention claimed herein.

EXAMPLES OF EMBODIMENTS

General Methodology

All the reagents and solvents are synthesis quality and are used without any additional treatment.

Abbreviations

The abbreviations used for amino acids follow the 1983 IUPAC-IUB Commission on Biochemical Nomenclature recommendations outlined in Eur. J. Biochem. (1984) 138: 9-37.

®, resin; 2-ClTrt-®, resin 2-chlorotrityl; 4-Abz, 4-aminobenzoic acid; Ac, acetyl; AM, 2-[4-aminomethyl-(2,4-dimethoxyphenyl)] phenoxyacetic acid; Asn, asparagine; Asp, aspartic acid; Boc, tert-butoxycarbonyl; C-terminal, carboxy-terminal; Cit, citrulline; DCM, dichloromethane; DIEA, N,N'-diisopropylethylamine or Hünig's base, DIPEA or DIEA; DIPCDI, N,N'-diisopropylcarbodiimide; DMF, N,N-dimethylformamide; equiv, equivalent; ES-MS, electrospray ionization mass spectrometry; Fmoc, 9-fluorenylmethyloxycarbonyl; Asp, aspartic acid; Val, valine; Lys, lysine; Tyr, tyrosine; 4-Abz, 4-aminobenzoic acid; Thr, threonine; Trp, tryptophan; Gln, glutamine; Gly, glycine; His, histidine; Cit, citrulline; Leu, leucine; Ile, isoleucine; Met, methionine; Orn, ornithine; Dbu, diaminobutyric acid; Dpr, diaminopropionic acid; HOBt, 1-hydroxybenzotriazole; HPLC, high performance liquid chromatography; Lys, lysine; MBHA, p-methylbenzhydrylamine; MeOH, methanol; N-terminal, amino-terminal; tBu, tert-butyl; TFA, trifluoroacetic acid; Thr, threonine; Trt, triphenylmethyl or trityl; Tyr, tyrosine; Val, valine; ECM, extracellular matrix; GAG, glycosaminoglycans; LOX, lysyl oxidase; LOXL, lysyl oxidase-like; MAGP; microfibril-associated glycoprotein; DANCE, developmental arteries and neural crest epidermal growth factor (EGF)-like; EVEC novel epidermal growth factor; EGF-like, epidermal growth factor, COPD, chronic obstructive pulmonary disease; DMEM-Glutamax; Dulbecco's Modified Eagle Medium; FBS, fragment-based screening; CV, Crystal Violet; RLU, relative light units; BMG, luminescence reader; DNA, deoxyribonucleic acid; TGF, transforming growth factor beta; HDFa, human dermal fibroblasts, adult; DAPI, 4',6-Diamidino-2-phenylindole dichlorohydrate; ELISA, Enzyme-Linked Immunosorbent Assay; BSA, Bis(trimethylsilyl)acetamide or phosphate buffered saline; GSEA, gene set enrichment analysis; OPD, o-Phenylenediamine; RNA, ribonucleic acid; COL, collagen; PLOD3, procollagen-lysine.

Chemical Synthesis

All synthetic processes were carried out in polypropylene syringes fitted with porous polyethylene discs or in glass reactors with a porous plate. All the reagents and solvents were synthesis quality and were used without any additional treatment. The solvents and soluble reagents were removed by suction. The Fmoc group was removed with piperidine-DMF (2:8, v/v) (1×1 min, 1×5 min; 5 mL/g resin) [Lloyd-Williams P. et al. (1997) "Chemical Approaches to the Synthesis of Peptides and Proteins" CRC, Boca Raton (Fla., USA)]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser E. et al., "Anal. Biochem". (1970) 34: 595-598] or chloranil [Christensen T. "Acta Chem. Scand." (1979), 33B: 763-766]. All synthetic reactions and washes were carried out at 25° C.

The HPLC chromatographic analysis was carried out with Shimadzu equipment (Kyoto, Japan) using a reversed-phase column thermostatized at 30° C. (250×4.6 mm, Kromasil® 100 $C_8$, 5 µm, Akzo Nobel, Sweden). The elution was carried out using a gradient of acetonitrile (+0.07% TFA) in water (+0.1% TFA) at a flow rate of 1 mL/min and detection was carried out at 220 nm. The electrospray ionization mass spectrometry analysis was carried out in a WATERS Alliance ZQ 2000 detector using a mixture of MeCN:$H_2O$ 4:1 (+0.1% TFA) as the mobile phase and a flow rate of 0.3 mL/min.

Example 1

Obtaining Ac-Gly-L-Gln-L-Lys(Ac-Gly-L-Gln)-4-Abz-$NH_2$ a) Obtaining Fmoc-L-Lys(Fmoc)-4-Abz-AM-MBHA-®

15 mmol of the resin pMBHA with a functionalization of 0.6 mmol/g were treated with 40% TFA in DCM (1×2 min+1×10 min+1×20 min), DCM (5×1 min) and a solution of 15% DIEA in DCM (3×2 min). The resin was washed with DCM (5×1 min) and DMF (3×1 min). 1.5 equiv of Fmoc-AM-OH were incorporated into the resin in the presence of 1.5 equiv of DIPCDI and 1.5 equiv of HOBt using DMF/DCM (1/1; v/v) as a solvent for 1 hour. The resin was then washed with DMF (3×1 min). The Fmoc N-terminal group was deprotected as described in the general methods (20% piperidine in DMF, 1×1 min+1×5 min). The resin was washed with DMF (5×1 min), after which 4 equiv of Fmoc-4-Abz-OH were incorporated in the presence of 4 equiv of DIPCDI and 4 equiv of HOBt using DMF as a solvent for 1 hour. It was filtered and the reaction was repeated adding 2 equiv of Fmoc-4-Abz-OH in the presence of 2 equiv of DIPCDI and 2 equiv of HOBt using DMF as a solvent for 19 hours. The resin was then washed as described in the general methods and the deprotection treatment of the Fmoc group was carried out to incorporate the following amino acid. 5 equiv of Fmoc-L-Lys(Fmoc)-OH were incorporated into the unprotected peptidyl resin in the presence of 5 equiv of DIPCDI and 5 equiv of HOBt using DMF as a solvent for 2 hours. It was filtered and the reaction was repeated applying 5 equiv of Fmoc-L-Lys (Fmoc)-OH in the presence of 5 equiv of DIPCDI and 5 equiv of HOBt using DMF as a solvent for 20 hours. The peptidyl resin was washed with DMF (5×1 min), DCM (4×1 min), diethyl ether (4×1 min) and was dried under vacuum.

b) Obtaining Ac-Gly-L-Gln-L-Lys(Ac-Gly-L-Gln)-4-Abz-AM-MBHA-®

The Fmoc N-terminal group of the peptidyl resin obtained in example 1.a) was deprotected as described in the general methods (20% piperidine in DMF, 1×1 min+1×5 min). 5 equiv of Fmoc-L-Gln-OH were incorporated into the unprotected resin in the presence of 5 equiv of DIPCDI and 10 equiv of HOBt using DMF as a solvent for 1 hour. The resin was then washed as described in the general methods and the deprotection treatment of the Fmoc group was carried out to incorporate the following amino acid. 5 equiv of Fmoc-Gly-OH were incorporated into the unprotected resin in the presence of 5 equiv of DIPCDI and 5 equiv of HOBt using DMF as a solvent for 1 hour. The resin was then washed as described in the general methods and the deprotection treatment of the Fmoc group was then repeated. Acetylation was carried out to the unprotected resin treating it with 5 equiv of $Ac_2O$ in the presence of 5 equiv of DIEA using DMF as a solvent for 30 min.

After the synthesis, the peptidyl resin was washed with DMF (5×1 min), DCM (4×1 min), diethyl ether (4×1 min) and was dried under vacuum.

c) Obtaining Ac-Gly-L-Gln-L-Lys(Ac-Gly-L-Gln)-4-Abz-$NH_2$ 7 g of dry peptidyl resin obtained in Example 1.b) were treated with 49 mL of TFA:$H_2O$ (95:5) for 2 hours at room temperature under stirring. It was filtered and the filtrate was collected on 350 mL cold diethyl ether. It was left to stand for 15 min and was centrifuged (10 min at 4000 rpm). The precipitates were decanted and washed with diethyl ether and centrifuged (5 min at 4000 rpm). The process of washing with diethyl ether was repeated again and the precipitates were dried under vacuum.

HPLC analysis of the obtained compound in gradients of MeCN (+0.07% TFA) in $H_2O$ (+0.1% TFA) showed a purity exceeding 80%. The identity of the compound obtained was confirmed by ES-MS.

TABLE 4

| Identifier | Average MW | Experimental MW |
|---|---|---|
| Ac-Gly-L-Gln-L-Lys(Ac-Gly-L-Gln)-4-Abz-$NH_2$ | 718.77 | 719.46 ± 0.91 |

Example 2

Obtaining Ac-L-Lys-L-His-L-Lys(Ac-L-Lys-L-His)-4-Abz-$NH_2$

This product was obtained according to the protocol described in example 1. The synthetic part was begun with 15 mmol of the resin pMBHA with a functionalization of 0.6 mmol/g and Fmoc-AM-OH (1.5 equiv), Fmoc-4-Abz-OH (4 equiv+2 equiv), Fmoc-L-Lys(Fmoc)-OH (2×5 equiv), Fmoc-L-His(Trt)-OH (5 equiv), Fmoc-L-Lys(Boc)-OH (5 equiv) and the Ac group (5 equiv) were incorporated respectively.

The cleavage of the polymeric carrier was carried out by treating 8.9 g of peptidyl resin with 62 mL of TFA:$H_2O$ (95:5) for 2 hours, for the precipitation 435 mL cold diethyl ether was used.

HPLC analysis of the compound obtained in gradients of MeCN (+0.07% TFA) in $H_2O$ (+0.1% TFA) showed a purity exceeding 80%. The identity of the compound obtained was confirmed by ES-MS.

TABLE 5

| Identifier | Average MW | Experimental MW |
|---|---|---|
| Ac-L-Lys-L-His-L-Lys(Ac-L-Lys-L-His)-4-Abz-$NH_2$ | 879.03 | 879.57 ± 0.60 |

Example 3

Obtaining Ac-L-Asn-L-Thr-L-Lys(Ac-L-Asn-L-Thr)-4-Abz-$NH_2$

This product was obtained according to the protocol described in example 1. The synthetic part was begun with 15 mmol of the resin pMBHA with a functionalization of 0.6 mmol/g and Fmoc-AM-OH (1.5 equiv), Fmoc-4-Abz-OH (4 equiv+2 equiv), Fmoc-L-Lys(Fmoc)-OH (2×5 equiv), Fmoc-L-Thr(tBu)-OH (5 equiv), Fmoc-L-Asn-OH (5 equiv) and the Ac group (5 equiv) were incorporated respectively.

The cleavage of the polymeric carrier was carried out by treating 7.5 g of peptidyl resin with 52 mL of TFA:$H_2O$ (95:5) for 2 hours, for the precipitation 365 mL cold diethyl ether was used.

HPLC analysis of the compound obtained in gradients of MeCN (+0.07% TFA) in $H_2O$ (+0.1% TFA) showed a purity exceeding 80%. The identity of the compound obtained was confirmed by ES-MS.

TABLE 6

| Identifier | Average MW | Experimental MW |
|---|---|---|
| Ac-L-Asn-L-Thr-L-Lys(Ac-L-Asn-L-Thr)-4-Abz-$NH_2$ | 778.82 | 778.92 ± 0.23 |

Example 4

Obtaining de Ac-L-Lys-L-Tyr-L-Lys(Ac-L-Lys-L-Tyr)-4-Abz-$NH_2$

This product was obtained according to the protocol described in example 1. The synthetic part was begun with 15 mmol of the resin pMBHA with a functionalization of 0.6 mmol/g and Fmoc-AM-OH (1.5 equiv), Fmoc-4-Abz-OH (4 equiv+2 equiv), Fmoc-L-Lys(Fmoc)-OH (2×5 equiv), Fmoc-L-Tyr(tBu)-OH (5 equiv), Fmoc-L-Lys(Boc)-OH (5 equiv) and the Ac group (5 equiv) were incorporated respectively.

The cleavage of the polymeric carrier was carried out by treating 8.2 g of peptidyl resin with 57 mL of TFA:$H_2O$ (95:5) for 2 hours, for the precipitation 400 mL cold diethyl ether were used.

HPLC analysis of the obtained compound in gradients of MeCN (+0.07% TFA) in $H_2O$ (+0.1% TFA) showed a purity exceeding 80%. The identity of the compound obtained was confirmed by ES-MS.

TABLE 7

| Identifier | Average MW | Experimental MW |
|---|---|---|
| Ac-L-Lys-L-Tyr-L-Lys(Ac-L-Lys-L-Tyr)-4-Abz-$NH_2$ | 931.10 | 929.65 ± 1.75 |

Example 5

Obtaining Ac-L-Lys-L-Cit-L-Lys(Ac-L-Lys-L-Cit)-4-Abz-$NH_2$

This product was obtained according to the protocol described in example 1. The synthetic part was begun with 15 mmol of the resin pMBHA with a functionalization of 0.6 mmol/g and Fmoc-AM-OH (1.5 equiv), Fmoc-4-Abz-OH (4 equiv+2 equiv), Fmoc-L-Lys(Fmoc)-OH (2×5 equiv), Fmoc-L-Cit-OH (5 equiv), Fmoc-L-Lys(Boc)-OH (5 equiv) and the Ac group (5 equiv) were incorporated respectively.

The cleavage of the polymeric carrier was carried out by treating 8.2 g of peptidyl resin with 57 mL of TFA:H$_2$O (95:5) for 2 hours, for the precipitation 400 mL cold diethyl ether were used.

HPLC analysis of the obtained compound in gradients of MeCN (+0.07% TFA) in H$_2$O (+0.1% TFA) showed a purity exceeding 80%. The identity of the compound obtained was confirmed by ES-MS.

TABLE 8

| Identifier | Average MW | Experimental MW |
|---|---|---|
| Ac-L-Lys-L-Cit-L-Lys(Ac-L-Lys-L-Cit)-4-Abz-NH$_2$ | 919.10 | 919.13 ± 0.24 |

Example 6

Obtaining Ac-L-Asp-L-Val-L-Lys-L-Tyr-OH (SEQ ID NO: 29)

a) Obtaining Ac-L-Asp(tBu)-L-Val-L-Lys(Boc)-L-Tyr(tBu)-O-2-ClTrt-®

33.6 mmol (1 equiv) of Fmoc-L-Tyr(tBu)-OH dissolved in 210 mL of DCM, to which 0.85 equiv of DIEA were added, were incorporated into the 2-chlorotrityl dry resin (21.0 g; 33.6 mmol). They were stirred for 5 min, after which 1.64 equiv of DIEA were added. It was left to react for 40 min. The remaining chloride groups were blocked by treatment with 17 mL of MeOH. Washes were carried out with DCM (3×1 min) and DMF (5×1 min). The N-terminal Fmoc group was deprotected by treatment with 5% piperidine in DCM/DMF (1/1; v/v) for 10 min followed by treatment with 20% piperidine in DMF (1×15 min). Washes were carried out with DMF (5×1 min) and 1.25 equiv of Fmoc-L-Lys(Boc)-OH was incorporated in the presence of 1.25 equiv DIPCDI and 1.25 equiv of HOBt for 1 hour. The resin was subsequently washed as described in the general methods.

The Fmoc N-terminal group was deprotected as described in the general methods and 1.25 equiv of Fmoc-L-Val-OH were incorporated into the peptidyl resin in the presence of 1.25 equiv of DIPCDI and 1.25 equiv of HOBt using DMF as a solvent for 1 hour. The resin was then washed as described in the general methods and the deprotection treatment of the Fmoc group was repeated to couple 1.25 equiv of Fmoc-L-Asp(tBu)-OH in the presence of 1.25 equiv of DIPCDI and 1.25 equiv of HOBt. The resin was then washed as described in the general methods and the deprotection treatment of the Fmoc group was repeated. Acetylation was carried out to the deprotected resin by treating it with 2.5 equiv of Ac$_2$O in the presence of 2.5 equiv of DIEA using DMF as a solvent for 30 min.

After the synthesis, the peptidyl resin was washed with DMF (5×1 min), DCM (4×1 min), diethyl ether (4×1 min) and was dried under vacuum.

b) Obtaining de Ac-L-Asp-L-Val-L-Lys-L-Tyr-OH 40.5 g of dry peptidyl resin were treated with 284 mL of TFA:H$_2$O (95:5) for 2 hours at room temperature under stirring. It was filtered and the filtrate was collected on 2.0 L cold diethyl ether. It was left to stand for 15 min and was filtered. Six washes were carried out with diethyl ether and the precipitates were dried under vacuum.

HPLC analysis of the obtained compounds in gradients of MeCN (+0.07% TFA) in H$_2$O (+0.1% TFA) showed a purity exceeding 80%. The identity of the compounds obtained was confirmed by ES-MS.

TABLE 9

| Identifier | Average MW | Experimental MW |
|---|---|---|
| Ac-L-Asp-L-Val-L-Lys-L-Tyr-OH | 565.62 | 564.52 ± 1.35 |

Example 7

Study of the Activation of the Human Fibulin-5 and LOXL1 Gene Promoters by Means of a High-Performance Luminescence Assay.

The effect of the compounds of the invention on the activity of the fibulin-5 and LOXL1 promoters was studied and compared to the levels of basal expression of the untreated cells (negative control) and with the effect of Interleukin-1β (IL-1β) in the same conditions.

Cells from an epithelial cell line doubly transfected with fibulin-5 and LOXL1 human promoters in which the luciferase gene is under the regulatory control of said promoters (4×10$^4$ cells/well) were seeded in a white plate and in a 96-well transparent plate, both treated with polylysine, and were incubated in Dulbecco's Modified Eagle Medium (DMEM-Glutamax™), with 10% of FBS, 1% Penicillin-Streptomycin (P/S), 1 mg/ml of Geneticin® (G418) and 2 µg/ml of for 24 hours at 37° C. in at atmosphere with 5% CO$_2$. After the incubation, the cells were incubated for 6 hours at 37° C. in at atmosphere with 5% CO$_2$ with DMEM without serum. Then, this medium was removed and the cells were treated with different compounds at 0.1 mg/ml, 0.5 mg/ml, 1 mg/ml or 2 mg/mL in DMEM/1% FBS for 16-24 hours. As a positive control to activate the fibulin-5 and LOXL1 promoters 10 ng/ml of IL-1β were used and as a negative control untreated cells were used, just with DMEM/1% FBS. The incubations and treatments were carried out in parallel in the white plate and the transparent plate and in triplicate for each condition. After the treatment, the relative light units per second were determined (RLU/s) in the white plate by means of consecutive quantification of the activities of Firefly luciferase (fibulin-5 promoter) and Renilla luciferase (LOXL1 promoter), and the number of total cells/well in the transparent plate by means of staining with Crystal Violet (CV). To determine the Firefly and Renilla luciferase activities the Dual-Glo Luciferase Assay System kit by Promega was used. The cells were briefly lysed and the Firefly luciferase substrate was added. After incubating for 10 min at 25° C., the RLU/s were quantified by luminescence reader (Lumistar-BMG). Then the Firefly signal was extinguished and the Renilla luciferase substrate was added. After incubating for 5 min at 25° C., the RLU/s were quantified by the same luminescence reader. With regard to the determination of the total number of cells by Crystal Violet, the CV dyes the DNA of the cells and the quantity of dye taken by the cells can be measured in an absorbency reader at 630 nm (Multiskan Ascent). The color obtained is directly proportional to the total number of cells per well. The cells were briefly incubated with 0.05% CV plus 4% Formalin for 20 minutes and after several washes with Milli-Q water, the cells were left to dry for 1-2 hours and then 0.1 M of HCl was added for its immediate reading. The RLU/s of the luciferases corresponding to each promoter were normalized by the average of the total number of cells per condition. Three independent assays with 3 measurements per assay were carried out for Ac-L-Asp-L-Val-L-Lys-L-Tyr-OH at 0.1 mg/mL and 1 mg/mL. 1 assay with 3 measurements was carried out for the other compounds and concentrations.

The increase in the activity of the promoters with regard to the levels of expression of the negative control was determined. The results showed that the product Ac-L-Asp-L-Val-L-Lys-L-Tyr-OH increases the basal activity of the fibulin-5 and LOXL1 promoters by 19% and 27%, respectively, at 1 mg/ml, as shown in table 10.

TABLE 10

Increase in the activity of the human promoters of the FIBULIN 5 and LOXL1 genes with regard to the negative control

| Product | | fibulin-5 (%) | LOXL1 (%) |
|---|---|---|---|
| 0.1 mg/mL | Ac-L-Asp-L-Val-L-Lys-L-Tyr-OH (SEQ ID NO. 29) | 7.46 | 7.12 |
| 1 mg/mL | Ac-L-Asp-L-Val-L-Lys-L-Tyr-OH (SEQ ID NO. 29) | 19.40 | 27.06 |
| 2 mg/mL | Ac-L-Asp-L-Val-L-Lys-L-Tyr-OH (SEQ ID NO. 29) | 53.20 | 10.41 |
| 2 mg/mL | H-L-Asp-L-Val-L-Lys-L-Tyr-OH (SEQ ID NO. 1) | 41.93 | 21.82 |
| 2 mg/mL | Ac-L-Asp-L-Val-L-Lys-L-Tyr-NH$_2$ (SEQ ID NO. 30) | 30.26 | 22.87 |
| 2 mg/mL | Palm-L-Asp-L-Val-L-Lys-L-Tyr-OH (Palm-SEQ ID NO. 1) | 32.47 | 25.17 |
| 2 mg/mL | Ac-L-Asp-L-Val-L-Lys-L-Tyr-NH(n-hexyl) (SEQ ID NO. 29-NH(n-hexyl)) | 18.11 | 7.54 |
| 2 mg/mL | Ac-L-Glu-L-Val-L-Lys-L-Tyr-OH (SEQ ID NO. 31) | 27.45 | 5.59 |
| 2 mg/mL | Ac-L-Gln-L-Val-L-Lys-L-Tyr-OH (SEQ ID NO. 32) | 19.79 | 22.61 |
| 2 mg/mL | Ac-L-Asp-L-Ile-L-Lys-L-Tyr-NH(n-hexadecyl) (Ac-SEQ ID NO. 5-NH(n-hexadecyl)) | 59.33 | 27.08 |
| 2 mg/mL | Ac-L-Asp-L-Leu-L-Lys-L-Tyr-OH (SEQ ID NO. 33) | 15.42 | 14.96 |
| 2 mg/mL | Ac-L-Asp-L-Met-L-Lys-L-Tyr-OH (SEQ ID NO. 34) | 14.36 | 32.85 |
| 2 mg/mL | Ac-L-Asp-L-Val-L-Orn-L-Tyr-OH (SEQ ID NO. 35) | 44.60 | 28.35 |
| 2 mg/mL | Ac-L-Asp-L-Val-L-Dbu-L-Tyr-OH (SEQ ID NO. 36) | 17.08 | 28.10 |

TABLE 10-continued

Increase in the activity of the human promoters of the FIBULIN 5 and LOXL1 genes with regard to the negative control

| Product | | fibulin-5 (%) | LOXL1 (%) |
|---|---|---|---|
| 2 mg/mL | Ac-L-Glu-L-Val-L-Lys-L-Trp-OH (SEQ ID NO. 37) | 10.92 | 22.22 |
| 2 mg/mL | Ac-L-Asn-L-Ile-L-Lys-L-Tyr-OH (SEQ ID NO. 38) | 12.25 | 9.83 |
| 2 mg/mL | H-L-Asn-L-Leu-L-Lys-L-Tyr-OH (SEQ ID NO. 16) | 9.69 | 16.67 |
| 2 mg/mL | Ac-L-Asn-L-Val-L-Dpr-L-Tyr-OH (SEQ ID NO. 39) | 35.49 | 3.99 |
| 2 mg/mL | Ac-L-Gln-L-Met-L-Lys-L-Tyr-OH (SEQ ID NO. 40) | 6.05 | 28.48 |
| 2 mg/mL | H-L-Gln-L-Val-L-Orn-L-Tyr-OH (SEQ ID NO. 41) | 7.04 | 25.84 |
| 2 mg/mL | Ac-L-Gln-L-Val-L-Lys-L-Trp-NH$_2$ (SEQ ID NO. 42) | 38.10 | 18.08 |
| 2 mg/mL | Ac-L-Asn-L-Ile-L-Dpr-L-Tyr-OH (SEQ ID NO. 43) | 41.79 | 8.75 |
| 2 mg/mL | Ac-L-Gln-L-Val-L-Dbu-L-Trp-NH$_2$ (SEQ ID NO. 44) | 26.39 | 68.94 |
| 2 mg/mL | H-L-Gln-L-Ile-L-Orn-L-Tyr-OH (SEQ ID NO. 27) | 4.41 | 47.99 |
| 1 mg/mL | Palm-L-Asn-L-Ile-L-Orn-L-Trp-NH(n-hexyl) (Palm-SEQ ID NO. 45-NH(n-hexyl)) | 43.65 | 18.48 |
| 0.5 mg/mL | Ac-Gly-L-Gln-L-Lys(Ac-Gly-L-Gln)-4-Abz-NH$_2$ | 17 | 79 |
| 0.5 mg/mL | Ac-Asn-L-His-L-Lys(Ac-Asn-L-His)-4-Abz-NH$_2$ | 53 | 47 |
| 0.5 mg/mL | Ac-Asn-L-Thr-L-Lys(Ac-Asn-L-Thr)-4-Abz-NH$_2$ | 39 | 51 |
| 0.5 mg/mL | Ac-Lys-L-Cit-L-Lys(Ac-Lys-L-Cit)-4-Abz-NH$_2$ | 21 | 22 |
| Positive control (10 ng/mL IL-1β) | | 80.40 | 156.26 |
| Negative control | | 0 | 0 |

Example 8

Study of the Increase in the Expression of the Proteins Fibulin-5 and LOXL1 in Human Dermal Fibroblasts by Means of Immunofluorescence Through Ac-L-Asp-L-Val-L-Lys-L-Tyr-OH (SEQ ID NO: 29).

In this experiment the number of times that the expression of the proteins fibulin-5 and LOXL1 in human dermal fibroblasts is increased with regard to the basal levels in untreated cells (negative control) when treating the cells with 0.5 mg/ml of the product Ac-L-Asp-L-Val-L-Lys-L-Tyr-OH and it is compared with the effect of Interleukin-1β (IL-1β) at 20 ng/ml and TGF-β at 5 ng/ml (positive controls), which increase an average of 1.5 times and 2 times, respectively, the expression of these proteins, in the same conditions.

Adult human dermal fibroblasts were seeded (HDFa) (2.5×10$^3$ cells/well) in a 96-well transparent plate, treated with polylysine, and were incubated in complete medium 106 for 72 hours at 37° C. in an atmosphere with 5% $CO_2$. After the incubation, the cells were treated with the different compounds in complete medium 106 for 48 hours at 37° C. in an atmosphere with 5% $CO_2$. As positive controls of increase of the expression of the proteins fibulin-5 and LOXL1, 5 ng/ml of TGF-β and 20 ng/ml of IL-1β were used and as a negative control untreated cells were used, just with complete medium 106. The incubations and the treatments were carried out in quadruplicate for each condition. After the treatment, the levels of expression of both proteins were quantified relatively by using specific fluorescent antibodies, photographic recording by microscopy and subsequent quantification of the fluorescent signal using image processing software, the number of total cells by fluorescent staining of the nuclei (DAPI) and subsequent quantification in the same images. For the determination of the expression of the proteins fibulin-5 and LOXL1 the cells were washed with PBS 48 hours after the treatments and were fixed with paraformaldehyde. Next, duplicates of each treatment were used to mark separately the fibulin-5 and LOXL1 proteins. For each of the proteins a specific primary monoclonal antibody was used (Abcam). After the primary incubation, the cells were washed with PBS and the secondary marking was carried out with specific fluorescent polyclonal antibodies for each primary antibody. For fibulin-5 an Alexa Fluor® 594 (red) secondary antibody was used and for LOXL1 an Alexa Fluor® 488 (green) secondary antibody was used. 16 hours later all the samples were stained with DAPI (4',6-Diamidino-2-Phenylindole), fluorescent marker for the staining of nuclei, and the photographic recording was carried out by fluorescence microscopy in a Leica microscope. 2-4 images were taken per condition and per protein and the fluorescent signals were quantified (IOD) corresponding to each protein and the nuclei by means of image analysis software. The fibulin-5 and LOXL1 signals were normalized according to the number of total nuclei for each image. 3 independent assays were carried out.

The results showed that the product Ac-L-Asp-L-Val-L-Lys-L-Tyr-OH increases the expression of fibulin-5 and LOXL1 by 134% and 73%, respectively, to 0.5 mg/ml, as shown in table 11.

TABLE 11

Increase in the expression of the proteins fibulin-5 and LOXL1 in human dermal fibroblasts with regard to the negative control

| Product | fibulin-5 (%) | LOXL1 (%) |
|---|---|---|
| 0.5 mg/mL Ac-L-Asp-L-Val-L-Lys-L-Tyr-OH | 133.90 | 72.71 |
| 5 ng/mL TGF-β | 147.72 | 45.93 |

TABLE 11-continued

Increase in the expression of the proteins fibulin-5 and LOXL1 in human dermal fibroblasts with regard to the negative control

| Product | fibulin-5 (%) | LOXL1 (%) |
|---|---|---|
| 20 ng/mL IL-1β | 42.07 | 87.50 |
| Negative control | 0 | 0 |

Example 9

Stimulation of Type-I Collagen Synthesis in Human Dermal Fibroblasts Through Ac-L-Asp-L-Val-L-Lys-L-Tyr-OH (SEQ ID NO: 29)

Type-I collagen is the principal collagen in the skin and is responsible for the resistance of this tissue.

Fibroblasts are the principal producers of collagen, therefore, in vitro quantification of collagen induced by cosmetic active ingredients provides information on their possible anti-wrinkle effect.

Stimulation of type-I collagen synthesis induced by cosmetic active ingredients was assessed by means of an ELISA (Enzyme-Linked Immunosorbent Assay) method.

Human dermal fibroblasts were trypsinized and seeded at a density of 5×10$^4$ cells/well in 48-well plates. After 24 hours of incubation at 37° C., 5% $CO_2$, with a humidified atmosphere, a new medium was added with 0.01 µg/mL Ac-L-Asp-L-Val-L-Lys-L-Tyr-OH. Untreated cells were used as negative controls. The cells were incubated for an additional 48 hours at 37° C., 5% $CO_2$, with humidified atmosphere. Subsequently, the medium was collected from each well to be analyzed by ELISA. A calibration curve with type-I collagen was prepared (Sigma) and the dilutions of this calibration curve were transferred to 96-well plates together with the mediums collected from the cells. The plates were left at 4° C. in a humid atmosphere for one night. Next the wells were washed three times with a washing solution prepared with PBS at 0.05% of Tween-20 (Sigma) and then any non-specific binding of the primary antibody with a solution of PBS at 3% BSA (sigma) was blocked. After the blocking, the wells were washed three times with the washing solution and the wells were incubated with an antibody against type-I collagen (Sigma) for 2 hours. After this incubation the wells were washed again and the secondary antibody IgG-HRP (Molecular Probes) was added for 1 hour. Once the incubation was completed the wells were washed and the OPD substrate (o-Phenylenediamine) (Sigma) was added and left to react for 30 minutes under stirring. The reaction was stopped adding a solution of $H_2SO_4$ 3 M and the absorbency reading was carried out at a wave length of 490 nm in a TECAN GENios spectrophotometric reader.

Table 12 presents the increase in type-I collagen synthesis with regard to the basal level of type-I collagen of the negative control.

TABLE 12

Determination of type-I collagen in human dermal fibroblasts with regard to the negative control

| PRODUCT | INCREASE IN SYNTHESIS OF TYPE-I COLLAGEN (%) |
|---|---|
| Negative control | 0 |
| 0.01 µg/ml Ac-L-Asp-L-Val-L-Lys-L-Tyr-OH | 47.3 |

Example 10

Study of the Profile of the Gene Expression of Human Dermal Fibroblasts

The number of times that sets of genes corresponding to different biological functions significantly increase is studied, within the gene profile of human dermal fibroblasts, with regard to the basal levels in untreated cells (negative control) by treatment with 0.05 mg/ml of the product Ac-L-Asp-L-Val-L-Lys-L-Tyr-OH (SEQ ID NO: 29). Adult human dermal fibroblasts (HDFa) were seeded ($12.5 \times 10^4$ cells/vial T25 cm$^2$), and were incubated in complete medium 106 for 7 days at 37° C. in an atmosphere with 5% $CO_2$. After the incubation, the cells were treated for 24 hours at 37° C. in an atmosphere with 5% $CO_2$ with 0.05 mg/ml of the compound Ac-L-Asp-L-Val-L-Lys-L-Tyr-OH in complete medium 106 or in complete medium 106 as a negative control. The incubations and the treatments were carried out in duplicate for each condition.

After the treatments, RNA was extracted and purified, the quality and quantity was verified and the marking was carried out as was the hybridization of the samples in a human gene expression microarray (ASurePrint G3, Agilent). With the data obtained from the microarray, the genes with differential expression were determined and a parametric analysis was carried out to determine the significantly differentially expressed genes compared with the negative control. Next an evaluation of the genes by means of GSEA was carried out to encompass these genes according to their function/biological route. 24 hours after the treatments, the cells were lysed and the RNA was extracted and purified from each replica and each condition by means of the RNeasyPlus Mini kit by Qiagen. The lysed cells were briefly homogenized and the RNases were inactivated. The samples were passed through special RNA binding columns and after several microcentrifugation washes to eliminate contaminants and impurities, the purified RNA was eluted with 50 µl of ultrapure water. The purity, integrity and concentration of the RNA obtained were evaluated by means of spectrophotometry (Nanodrop) and with a bioanalyzer (Agilent Bioanalyzer).

The normalized values obtained with the treatment were compared with the normalized values obtained with the negative control to obtain genes with differential expression. Next, a parametric analysis of the data was carried out by means of the Bioconductor software and the genes are considered to be significantly expressed for a value of <0.05. The values obtained are also evaluated by means of GSEA (Gene Set Analysis Enrichment) to group together the genes with differential expression in terms of Gene Ontology and Biological Routes and the sets of genes with an expected proportion of incorrectly rejected null hypotheses were selected as significant (FDR) <25%. The results obtained are shown below in three different tables in which different families of genes are grouped together (collagen genes, genes involved in collagen synthesis and genes involved in cell adhesion).

TABLE 13

Collagen genes overexpressed by the compound Ac-L-Asp-L-Val-L-Lys-L-Tyr-OH

| Symbol | Name | % Expression induction |
|---|---|---|
| COL11A1 | Collagen, type-XI, alpha 1 | 7.2 |
| COL22A1 | Collagen, type-XXII, alpha 1 | 7.7 |
| COL4A2 | Collagen, type-IV, alpha 2 | 8.3 |
| COL27A1 | Collagen, type-XXVII, alpha 1 | 14.2 |
| COL6A2 | Collagen, type-VI, alpha 2 | 16.0 |
| COL6A3 | Collagen, type-VI, alpha 3 | 18.6 |
| COL4A1 | Collagen, type-IV, alpha 1 | 18.9 |
| COL1A2 | Collagen, type-I, alpha 2 | 31.1 |
| COL14A1 | Collagen, type-XIV, alpha 1 | 36.1 |

TABLE 14

Genes involved in collagen synthesis overexpressed by the compound Ac-L-Asp-L-Val-L-Lys-L-Tyr-OH

| Symbol | Name | % Expression induction |
|---|---|---|
| PLOD3 | Procollagen-lysine, 2-oxoglutarate 5-dioxygenase 3 | 20.7 |
| PCOLCE | Procollagen C-endopeptidase enhancer | 22.4 |
| SERPINH1 | Serpin peptidase inhibitor, class H (heat shock protein 47), member 1, (collagen binding protein 1) | 25.3 |

TABLE 15

Genes involved in cell adhesion overexpressed by the compound Ac-L-Asp-L-Val-L-Lys-L-Tyr-OH

| Symbol | Name | % Expression induction |
|---|---|---|
| VCL | Vinculin | 4.2 |
| CAPNS2 | Calpain, small subunit 2 | 17.9 |
| CAPNS1 | Calpain, small subunit 1 | 22.1 |
| ROCK1 | Rho-associated, coiled-coil containing protein kinase 1 | 22.7 |
| ACTN1 | Actinin, alpha 1 | 27.4 |
| TLN1 | Talin 1 | 27.5 |
| GSN | Gelsolin | 30.1 |
| ITGB1 | Integrin, beta 1 (fibronectin receptor, beta polypeptide, antigen CD29 includes MDF2, MSK12) | 33.0 |
| ZYX | Zyxin | 35.7 |
| PFN1 | Profilin 1 | 36.8 |

Example 11

Stimulation of Elastin Synthesis in Human Dermal Fibroblasts Through Ac-L-Asp-L-Val-L-Lys-L-Tyr-OH (SEC? ID NO: 29)

Elastin is a protein which forms parts of the connective tissue with elastic properties and which helps to keep the skin flexible but firm. Fibroblasts are the principal producers of elastin, therefore, in vitro quantification of elastin induced by cosmetic active ingredients provides information on its effect on the improvement to the elasticity of the skin.

Stimulation of elastin synthesis induced by Ac-L-Asp-L-Val-L-Lys-L-Tyr-OH was evaluated by means of a quantitative method of staining, Fastin Elastin Assay (Tebu-Bio). Human dermal fibroblasts were trypsinized and seeded at a density of $7 \times 10^4$ cells/well in 6-well plates. After 72 hours of incubation at 37° C., 5% $CO_2$, with a humidified atmosphere, a new medium was added with 0.01 μg/mL Ac-L-Asp-L-Val-L-Lys-L-Tyr-OH. Untreated cells were used as negative controls and cells treated with TGF-1β (Peprotech) were used as positive controls. The cells were incubated for an additional 48 hours at 37° C., 5% $CO_2$, with humidified atmosphere. Subsequently, the elastin was solubilized and extracted, for which the cells were washed twice with PBS (Sigma) and a solution was added to uncouple the cells (Cell Dissociation Solution, Sigma). The suspension of cells was transferred to centrifuge tubes, 1 M Oxalic Acid was added provided by the kit and they were incubated at 100° C. for 1 hour. Once the elastin became soluble, a calibration curve was prepared with the elastin provided with the kit. From that point, the samples and dilutions of the calibration curve were processed following the kit instructions to isolate and stain the elastin. Lastly, the dye was extracted and the absorbency reading was carried out at a wave length of 540 nm in a TECAN GENios spectrophotometric reader. Table 16 presents the percentage of elastin with regard to that observed in the negative controls.

TABLE 16

Determination of elastin in human dermal fibroblasts with regard to the negative control

| PRODUCT | INCREASE IN ELASTIN SYNTHESIS (%) |
|---|---|
| Negative control | 0% |
| 10 ng/mL TGF-1β | 35.6% |
| 0.01 μg/ml Ac-L-Asp-L-Val-L-Lys-L-Tyr-OH | 21.7% |

Example 12

Preparation of an Aqueous Solution of the Compound Ac-L-Asp-L-Val-L-Lys-L-Tyr-OH (SEQ ID NO: 29)

In a suitable vessel CAPRYLYL GLYCOL is dissolved by heating it to 40° C. until it is perfectly dissolved, after which the compound Ac-L-Asp-L-Val-L-Lys-L-Tyr-OH is added stirring until it is completely dissolved. Lastly, the pH is adjusted with sodium hydroxide (INCI: SODIUM HYDROXIDE).

TABLE 17

Aqueous solution of the compound Ac-L-Asp-L-Val-L-Lys-L-Tyr-OH

| Phase | INGREDIENT | % in weight |
|---|---|---|
| A | WATER (AQUA) | qsp 100 |
| A | CAPRYLYL GLYCOL | 0.5 |
| A | Ac-L-Asp-L-Val-L-Lys-L-Tyr-OH | 0.05 |
| A | SODIUM HYDROXIDE | 0.0035 |

Example 13

Preparation of a Microemulsion of the Compound Ac-L-Asp-L-Val-L-Lys-L-Tyr-OH (SEQ ID NO: 29)

In a suitable vessel Docusate Sodium USP [INCI: DIETHYLHEXYL SODIUM SULFOSUCCINATE] and isostearic acid [INCI: ISOSTEARIC ACID] (phase A) were mixed together. In another vessel the compound Ac-L-Asp-L-Val-L-Lys-L-Tyr-OH was dissolved in water [INCI: WATER (AQUA)] (phase B). Phase B was slowly added to phase A under stirring. See Table 18.

TABLE 18

Microemulsion of the compound Ac-L-Asp-L-Val-L-Lys-L-Tyr-OH

| Phase | INGREDIENT | % in weight |
|---|---|---|
| A | DIETHYLHEXYL SODIUM SULFOSUCCINATE | 13.46 |
| A | ISOSTEARIC ACID | 76.29 |
| B | Ac-L-Asp-L-Val-L-Lys-L-Tyr-OH | 0.01 |
| B | WATER (AQUA) | 10.00 |

Example 14

Preparation of a Composition of Lipid Nanoparticles Containing the Microemulsified Compound Ac-L-Asp-L-Val-L-Lys-L-Tyr-OH (SEQ ID NO: 29).

In a suitable vessel the following ingredients were added in this order: water [INCI: WATER (AQUA)], Amigel® [INCI: SCLEROTIUM GUM], Zemea™ [INCI: PROPANEDIOL] and phenoxyethanol [INCI: PHENOXYETHANOL] (phase A ingredients), and was stirred until fully homogenized.

In another vessel, the microemulsion of the compound prepared according to example 1, refined soybean oil IP Ph. Eur. [INCI: *GLYCINE SOJA* (SOYBEAN) OIL], Arlacel 83V™ [INCI: SORBITAN SESQUIOLEATE], and Arlamol™ HD [INCI: ISOHEXADECANE] were added (phase B ingredients).

Then, the mixture of ingredients B was added to the mixture of ingredients A, under turbine stirring until an emulsion was formed.

The sample was homogenized using a Vibra Cell™ ultrasonic probe owned by Sonics Material for 30 seconds.

Then, Sensomer™ CI 50 [INCI: WATER (AQUA), STARCH HYDROXYPROPYLTRIMONIUM CHLORIDE, UREA, SODIUM LACTATE, SODIUM CHLORIDE, SODIUM BENZOATE] was added (phase C). See Table 19.

TABLE 19

Lipid nanoparticles containing the compound Ac-L-Asp-L-Val-L-Lys-L-Tyr-OH

| Phase | INGREDIENT | % in weight |
|---|---|---|
| A | WATER (AQUA) | q.s.p.100 |
| A | SCLEROTIUM GUM | 0.50 |
| A | PROPANEDIOL | 5.00 |
| A | PHENOXYETHANOL | 2.6 |
| B | MICROEMULSION FROM EXAMPLE 2 | 10 |
| B | *GLYCINE SOJA* (SOYBEAN) OIL | 12.00 |
| B | SORBITAN SESQUIOLEATE | 4.30 |
| B | ISOHEXADECANE | 5.50 |
| C | WATER (AQUA), STARCH HYDROXYPROPYLTRIMONIUM CHLORIDE, UREA, SODIUM LACTATE, SODIUM CHLORIDE, SODIUM BENZOATE | 0.20 |

Example 15

Obtaining Liposomes Containing the Compound Ac-L-Asp-L-Val-L-Lys-L-Tyr-OH (SEQ ID NO: 29).

In a suitable vessel the compound Ac-L-Asp-L-Val-L-Lys-L-Tyr-OH was added to water [INCI: WATER (AQUA)] and sodium salicylate [INCI: SODIUM SALICYLATE], so phase A was obtained. Water, Zemea™ [INCI: PROPANEDIOL] and phenoxyethanol [INCI: PHENOXYETHANOL] (phases B a D) were added to this phase. When all the previous components had been dissolved, then Leciflor™ 100 IP [INCI: LECITHIN] (phase E) was added little by little under intense stirring until complete solution. Afterwards Labrasol® [INCI: PEG-8 CAPRYLIC/CAPRIC GLYCERIDES] (phase F) was added and was left stirring for 10-15 minutes to form an emulsion.

TABLE 20

Lipid nanoparticles containing the compound Ac-L-Asp-L-Val-L-Lys-L-Tyr-OH

| Phase | INGREDIENT | % in weight |
|---|---|---|
| A | WATER (AQUA) | 10 |
| A | SODIUM SALICYLATE | 0.03 |
| A | Ac-L-Asp-L-Val-L-Lys-L-Tyr-OH | 0.01 |
| B | WATER (AQUA) | qsp 100 |
| C | PROPANEDIOL | 8.50 |
| D | PHENOXYETHANOL | 1.70 |
| E | LECITHIN | 10.00 |
| F | PEG-8 CAPRYLIC/CAPRIC GLYCERIDES | 4.00 |

The sample was homogenized using a Vibra Cell™ ultrasonic probe from Sonics Material for 30 seconds.

Example 16

Preparation of a Cosmetic Facial Serum Containing Ac-L-Asp-L-Val-L-Lys-L-Tyr-OH (SEQ ID NO: 29)

In a suitable vessel for the whole content, the components of phase A are added. Once they have been dissolved in water, A1 is added little by little under stirring with a rotor until complete dispersion. Straight away after this, A2 is added little by little under stirring with a rotor until complete dispersion. Once A1 and A2 have been dispersed the components from B are added and stirred until complete dispersion, after which the components from C are added and then the perfume from phase D. Lastly, the pH is adjusted with SODIUM HYDROXIDE (INCI: SODIUM HYDROXIDE) to pH 6.0.

TABLE 21

Cosmetic facial serum

| Phase | INGREDIENT | % in weight |
|---|---|---|
| A | WATER (AQUA) | qsp 100 |
| A | PROPANEDIOL | 10 |
| A | GLYCERETH-26 | 3 |
| A | DERMOSOFT ® OM (INCI: METHYLPROPANEDIOL, CAPRYLYL GLYCOL) | 2 |
| A | DERMOSOFT ® MCA (INCI: CAPRYLYL GLYCOL, DIPROPYLENE GLYCOL, GLYCERYL CAPRYLATE) | 0.5 |
| A | DISODIUM EDTA | 0.3 |
| A1 | CARBOMER | 0.15 |
| A2 | LECIGEL ™ (INCI: SODIUM ACRYLATES COPOLYMER, LECITHIN) | 2 |
| B | CAPRYLIC CAPRIC TRIGLYCERIDES | 3 |
| B | TRIETHYLHEXANOIN | 3 |
| B | TOCOPHERYL ACETATE | 0.5 |
| C | ADIFYLINE ® SOLUTION (INCI: BUTYLENE GLYCOL, WATER (AQUA), HEXAPEPTIDE-38) | 2 |
| C | AQUEOUS SOLUTION FROM EXAMPLE 12 | 2 |
| D | FRAGRANCE (PARFUM) | 0.15 |
| E | SODIUM HYDROXIDE | qsp pH 6.0 |

Example 17

Preparation of a Cosmetic Body Cream Containing Ac-L-Asp-L-Val-L-Lys-L-Tyr-OH (SEQ ID NO: 29)

In a suitable vessel for the whole contents phase A is weighed and stirred with the help of a rotor. A1 is added to the previous step and stirred with the help of a rotor until it is completely dispersed. A2 is added to the previous step and stirred with the help of a rotor. This step is heated to 75° C. to carry out the emulsion. Phase B is premixed and dissolved in the bath at 75° C., and added to the previous step under stirring with a turbine to carry out the emulsion. At approx. 50° C., C is added one by one, stirring with a turbine. Once at room temperature D is added, stirring with a rotor. Lastly, the pH is adjusted to 6.0-6.5 with E.

TABLE 22

Cosmetic body cream

| Phase | INGREDIENT | % in weight |
|---|---|---|
| A | WATER (AQUA) | qsp 100 |
| A | PROPANEDIOL | 10 |
| A | GLYCERETH-26 | 5 |
| A | DERMOSOFT ® OM (INCI: METHYLPROPANEDIOL, CAPRYLYL GLYCOL) | 2 |
| A | DERMOSOFT ® MCA (INCI: CAPRYLYL GLYCOL, DIPROPYLENE GLYCOL, GLYCERYL CAPRYLATE) | 0.5 |
| A | DISODIUM EDTA | 0.3 |
| A1 | SODIUM CARBOMER | 0.3 |
| A2 | ACRYLATES/VINYL ISODECANOATE CROSSPOLYMER | 0.2 |
| B | C12-15 ALKYL BENZOATE | 9 |
| B | PROPYLENE GLYCOL DICAPRYLATE/DICAPRATE | 3 |
| B | SODIUM STEAROYL LACTYLATE | 2 |
| B | POLYGLYCERYL-3 STEARATE | 2 |
| B | SHEA BUTTER (BUTYROSPERMUM PARKII) | 1 |
| B | TOCOPHERYL ACETATE | 0.5 |
| C | AQUEOUS SOLUTION FROM EXAMPLE 12 | 2 |
| C | SERILESINE ® SOLUTION GC (INCI: WATER (AQUA), GLYCERIN, HEXAPEPTIDE-10, CAPRYLYL GLYCOL) | 1 |
| D | FRAGRANCE (PARFUM) | 0.15 |
| E | SODIUM HYDROXIDE | qsp pH 6.0 |

Example 18

Preparation of a Cosmetic Facial Cream Containing Ac-L-Asp-L-Val-L-Lys-L-Tyr-OH (SEQ ID NO: 29)

In a suitable vessel for the whole contents phase A is weighed and stirred with the help of a rotor. A1 and A2 are added to the previous step and stirred with the help of a rotor. This step is heated to 75° C. to carry out the emulsion. Phase B is premixed in another vessel and dissolved in the bath at 75° C., and added to the previous step under stirring with a turbine to carry out the emulsion. At 50° C., C is added, stirring with a turbine. Once at room temperature D is added, stirring with a rotor, after which the pH is adjusted to 6.0-6.5 with F if necessary.

TABLE 23

Cosmetic facial cream

| Phase | INGREDIENT | % in weight |
|---|---|---|
| A | WATER (AQUA) | qsp 100 |
| A | PROPANEDIOL | 10 |
| A | GLYCERETH-26 | 5 |
| A | DERMOSOFT ® OM (INCI: METHYLPROPANEDIOL, CAPRYLYL GLYCOL) | 2 |

TABLE 23-continued

Cosmetic facial cream

| Phase | INGREDIENT | % in weight |
|---|---|---|
| A | DERMOSOFT ® MCA (INCI: CAPRYLYL GLYCOL, DIPROPYLENE GLYCOL, GLYCERYL CAPRYLATE) | 0.5 |
| A | DISODIUM EDTA | 0.3 |
| A1 | SODIUM CARBOMER | 0.3 |
| A2 | ACRYLATES/VINYL ISODECANOATE CROSSPOLYMER | 0.2 |
| B | C12-15 ALKYL BENZOATE | 9 |
| B | SODIUM STEAROYL LACTYLATE | 2 |
| B | POLYGLYCERYL-3 STEARATE | 2 |
| B | SHEA BUTTER (*BUTYROSPERMUM PARKII*) | 1 |
| B | TOCOPHERYL ACETATE | 0.5 |
| C | AQUEOUS SOLUTION FROM EXAMPLE 12 | 2 |
| C | SERILESINE ® SOLUTION GC (INCI: WATER (AQUA), GLYCERIN, HEXAPEPTIDE-10, CAPRYLYL GLYCOL) | 1 |
| D | SEPIGEL ™ 305 (INCI: POLYACRYLAMIDE, WATER (AQUA), C13-14 ISOPARAFFIN, LAURETH-7) | 2 |
| E | FRAGRANCE (PARFUM) | 0.15 |
| F | SODIUM HYDROXIDE | qsp pH 6.0 |

Example 19

Preparation of a Cosmetic Composition Containing Ac-L-Asp-L-Val-L-Lys-L-Tyr-OH (SEQ ID NO: 29)

In a suitable vessel the components from phase A are dissolved until PENTYLENE GLYCOL and BENZYL ALCOHOL are completely dissolved, after which A1 and A2 are added under stirring until completely dissolved. Once they have been incorporated, the mixture is heated to 70-75° C. Separately, the components from B are mixed together and heated to 70-75° C., after which B is added to A little by little and under stirring with a turbine. It is stirred until the temperature reaches 35-40° C., after which C is added, stirring whilst the cream gains viscosity. Once it is at room temperature, D is added under stirring. Lastly, the pH is adjusted to 6.0-6.5 with E and the aqueous solution of Ac-L-Asp-L-Val-L-Lys-L-Tyr-OH described in example X (phase F) is added.

TABLE 24

Cosmetic composition containing Ac-L-Asp-L-Val-L-Lys-L-Tyr-OH

| Phase | INGREDIENT | % in weight |
|---|---|---|
| A | WATER (AQUA) | QSP 100 |
| A | PENTYLENE GLYCOL | 5 |
| A | BENZYL ALCOHOL | 1 |
| A1 | CARBOMER | 0.5 |
| A2 | POTASSIUM CETYL PHOSPHATE | 0.5 |
| B | PHYTOCREAM ® 2000 (INCI: GLYCERYL STEARATE, CETEARYL ALCOHOL, POTASSIUM PALMITOYL HYDROLYZED WHEAT PROTEIN) | 5 |
| B | C12-15 ALKYL BENZOATE | 4 |
| B | ETHYLHEXYL COCOATE | 2.5 |
| B | SHEA BUTTER (*BUTYROSPERMUM PARKII*) | 2 |
| B | DIMETHICONE | 1 |
| B | PHENOXYETHANOL | 0.9 |
| B | TOCOPHERYL ACETATE | 0.5 |
| C | SEPIGEL ™ 305 (INCI: POLYACRYLAMIDE, WATER (AQUA), C13-14 ISOPARAFFIN, LAURETH-7) | 1 |
| D | PARFUM (FRAGRANCE) | 0.1 |
| E | SODIUM HYDROXIDE | qsp pH 6.0-6.5 |
| F | AQUEOUS SOLUTION FROM EXAMPLE 12 | 2 |

Example 20

In Vivo Effectiveness of Cosmetic Facial Cream Containing Ac-L-Asp-L-Val-L-Lys-L-Tyr-OH (SEQ ID NO: 29)

The aim of the study is to evaluate and compare the in vivo effectiveness of a product for cutaneous sagging (loss of firmness) with a placebo.

The study lasted 55 days with measurement at initial time and at the end of the 55 days. The panel was formed by 20 volunteers, Caucasian women, between the ages of 50 and 60, treated with the cream containing the compound Ac-L-Asp-L-Val-L-Lys-L-Tyr-OH from example 13 on one half of the face and a placebo cream (the same as the one from example 13, but without the compound Ac-L-Asp-L-Val-L-Lys-L-Tyr-OH on the other half of the face. The product was applied twice a day, in the morning and at night. The study was carried out double blind, comparative (the results obtained on one half of the face are compared with those obtained on the other half of the face) and where each volunteer serves as their own reference (the results obtained at different times are compared with those obtained at T0).

The evaluation is carried out by means of two different techniques that are described below:
1) In vivo confocal microscopy on the cheek area: the objective of this technique is to quantify, in vivo and in a standard fashion, the tisular structure of the reticular surface of the dermis at two levels: a first level in the upper area of the layer and the second at 25 μm depth (average) with regard to the first. Thanks to this protocol, the change in the network of fibers and the fragmentation rates at different levels of depth of the superficial reticular dermis can be measured (FRAGABIS parameter).
2) Ballistometry in the cheek area: the principle of ballistometry is based on the use of an impacting mass on the surface of the skin to measure its mechanical properties through interaction. In simple terms, a vibrational movement is imposed on the skin through the ballistometer hammer impacting on the skin. The ricochets induced, recorded over 3 seconds, are translated into electric signals which can be quantified and evaluated in terms of amplitude. These measurements enable the skin's firmness to be evaluated. The values measured are: Indentation, depth of penetration of the mass on the first impact. This value measures the firmness of the sample but is not relative to the elasticity. On the other hand, the Area between the profile of the ricochet and the initial value of the sample before impact.

The results of the test are shown in table 25 and 26:

TABLE 25

In vivo effectiveness of cosmetic facial cream containing Ac-L-Asp-L-Val-L-Lys-L-Tyr-OH (Confocal microscopy) vs. Initial time

| PRODUCT | Level of fragmentation for the upper reticulum (upper FRAGABIS) | Level of fragmentation for the deep reticulum (deep FRAGABIS) |
|---|---|---|
| Negative control (placebo) | −0.8% | 12.7% |
| Cream with Ac-L-Asp-L-Val-L-Lys-L-Tyr-OH | −39.6% | −37.9% |

TABLE 26

In vivo effectiveness of a cosmetic facial cream containing Ac-L-Asp-L-Val-L-Lys-L-Tyr-OH (Confocal microscopy) vs. Initial time

| PRODUCT | Indentation | Area |
|---|---|---|
| Cream with Ac-L-Asp-L-Val-L-Lys-L-Tyr-OH | −9.5% | −23.2% |

The invention claimed is:

1. A compound of general formula (I):

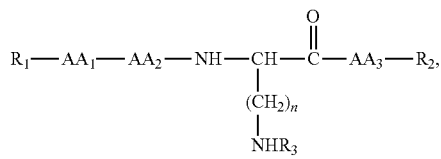

its stereoisomers, mixtures thereof and/or its cosmetic or pharmaceutical acceptable salts, wherein:

$AA_1$ is selected from the group consisting of -Asp-, -Glu-, -Asn-, -Gln-, -Lys- and -Gly-;

$AA_2$ is selected from the group consisting of -Val-, -Leu-, -Ile-, -Met-, -Cit-, -His-, -Thr- and -Gln -;

$AA_3$ is selected from the group consisting of -Tyr-, -Trp- and 4-Aminobenzoyl (-4-Abz);

n is selected from 1, 2, 3 and 4;

$R_3$ is selected from the group consisting of H and -$AA_2$-$AA_1$-$R_1$;

$R_1$ is selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, substituted or unsubstituted aralkyl and $R_6$—CO—, wherein $R_6$ is selected from the group consisting of H, substituted or unsubstituted non-cyclic aliphatic groups, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —$NR_4R_5$, —$OR_4$ and —$SR_4$, wherein $R_4$ and $R_5$ are independently selected from the group consisting of H, a polymer derived from polyethylene glycol, substituted or unsubstituted non-cyclic aliphatic groups, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and $R_2$ are not α-amino acids, with the condition that if $R_3$ is H, then $AA_2$ is selected from the group consisting of -Val-, -Leu-, -Ile- and -Met-, and $AA_1$ is selected from the group consisting of -Asp-, -Glu-, -Asn- and -Gln-.

2. The compound according to claim 1, wherein $AA_1$ is selected from the group consisting of -Asp-, -Glu-, -Asn- and -Gln-, $AA_2$ is selected from the group consisting of -Val-, -Leu-, -Ile- and -Met-, $R_3$ is H, and $AA_3$ is -Tyr- or -Trp-.

3. The compound according to claim 1, wherein $AA_1$ is selected from the group consisting of -Lys-, -Gly- and -Asn-, $AA_2$ is selected from the group consisting of -His-, -Thr-, -Gln-, and -Cit- and $AA_3$ is 4-Abz.

4. The compound according to claim 1 wherein $R_1$ is selected from the group consisting of H, acetyl, lauroyl, myristoyl and palmitoyl, $AA_1$ is -L-Asp-, $AA_2$ is -L-Val- and $AA_3$ is -L-Tyr-, $R_3$ is H, n is 4 and $R_2$ is selected from the group consisting of —$NR_4R_5$ and —$OR_4$ wherein $R_4$ and $R_5$ are independently selected from H, methyl, ethyl, hexyl, dodecyl and hexadecyl.

5. A cosmetic or pharmaceutical composition which comprises at least one compound of general formula (I), its stereoisomers, mixtures thereof and/or its cosmetically or pharmaceutically acceptable salts, according to claim 1, together with at least one cosmetically or pharmaceutically acceptable excipient or adjuvant.

6. The composition according to claim 5, wherein said compound of general formula (I), its stereoisomers, mixtures thereof and/or its cosmetically or pharmaceutically acceptable salts, is incorporated into a cosmetic or pharmaceutically acceptable delivery system or sustained release system selected from the group consisting of liposomes, mixed liposomes, oleosomes, niosomes, ethosomes, milliparticles, microparticles, nanoparticles, solid lipid nanoparticles, nanostructured lipid carriers, sponges, cyclodextrins, vesicles, micelles, mixed micelles of surfactants, surfactant-phospholipid mixed micelles, millispheres, microspheres, nanospheres, lipospheres, millicapsules, microcapsules, nanocapsules, microemulsions and nanoemulsions or is absorbed onto an organic solid polymer or solid mineral support selected from the group consisting of talc, bentonite, silica, starch and maltodextrin.

7. The composition according to claim 5, wherein said composition is in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils, sprays, aerosols, capsules, gelatin capsules, soft capsules, hard capsules, tablets, sugar coated tablets, tablets, pills, powders, granules, chewing gum, solutions, suspensions, emulsions, syrups, elixirs, jellies and gelatins.

8. The composition according to claim 5, wherein said composition also comprises at least one cosmetically or pharmaceutically acceptable adjuvant selected from the group consisting of agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, lamin in synthesis-stimulating agents, defensin synthesis-stimulating agents, chaperone synthesis-stimulating agents, cAMP synthesis-stimulating agents, AQP-3 modulating agents, aquaporin synthesis-modulating agents, proteins from the aquaporin family, hyaluronic acid synthesis-stimulating agents, glycosaminoglycan synthesis-stimulating agents, fibronectin synthesis-stimulating agents, sirtuin synthesis-stimulating agents, agents activating sirtuins, heat shock proteins, heat shock protein synthesis-stimulating agents, agents stimulating the synthesis of lipids and components of the stratum corneum, ceramides, fatty acids, agents that inhibit collagen degradation, agents that inhibit matrix metalloproteases, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, DNA protecting agents, DNA repair agents, stem cell protecting agents, agents for the treatment and/or care of sensitive skin, agents with firming and/or redensifying and/or restructuring activity, anti-stretch mark agents, agents inhibiting neuronal exocytosis, anticholinergic agents, agents inhibiting muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor aggregation, agents inhibiting acetylcholinesterase, dermo-relaxant agents, melanin synthesis inhibiting or stimulating agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, detoxifying agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments, colorants, dyes, biopolymers, gelling polymers, thickening agents, surfactants, softening agents, emulsifiers, binding agents, preservatives, agents able to reduce or treat bags under the eyes, exfoliating agents, keratolytic agents, desquamating agents, antimicrobial agents, antifungal agents, fungistatic agents, bactericidal agents, bacteriostatic agents, antihyperkeratosis agents, comedolytic agents, anti-psoriatic agents, stabilizers, astringents, agents regulating sebum production, lipolytic agents or agents stimulating lipolysis, adipogenic agents, agents modulating PGC-1 α, agents modulating PPARγ, agents which increase or reduce the triglyceride content of adipocytes, anti-cellulite agents, agents inhibiting PAR-2 activity, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents inhibiting vascular permeability, venotonic agents, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor masking antiperspirants, chelating agents, plant extracts, essential oils, marine extracts, agents obtained from a biofermentation process, mineral salts, cell extracts, sunscreens and organic or mineral photoprotective agents active against ultraviolet A and/or B rays and/or infrared A rays, and mixtures thereof.

9. A method of treatment of chronic obstructive pulmonary disease, urinary incontinence, degradation of the elastic lamina of the Brunch membrane, cutis laxa, pelvic organ prolapse, age-related macular degeneration and/or diabetic retinopathy comprising administering the compound of general formula (I), its stereoisomers, mixtures thereof and/or its cosmetically or pharmaceutically acceptable salts, according to claim 1, to contact a site of a mammal's body.

10. The method according to claim 9, wherein the treatment includes applying the compound to the skin.

11. The method according to claim 10, wherein the treatment is a cosmetic, non-therapeutic treatment and/or care of the skin.

12. The method of claim 10, wherein the treatment is a treatment of aging and/or photoaging of the skin.

13. The method of claim 10, wherein the treatment is to increase the elasticity and/or firmness of the skin, and/or to stimulate collagen and/or elastin synthesis.

14. A method of treatment for stimulation of the synthesis of LOXL-1 and/or fibulin-5 comprising administering the compound of general formula (I), its stereoisomers, mixtures thereof and/or its cosmetically or pharmaceutically acceptable salts, according to claim 1, to contact a site of a mammal's body.

15. The method of claim 9, wherein the administration of the compound is carried out topically, transdermally, orally or parenterally.

16. The method of claim 15, wherein the administration of the compound is by topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

17. A method of treatment and/or care of the skin to stimulate the synthesis of LOXL-1 and/or fibulin-5 comprising administration to the skin of a composition comprising a cosmetically or pharmaceutically effective quantity of at least one compound of general formula (I), its stereoisomers, mixtures thereof and/or its cosmetically or pharmaceutically acceptable salts of claim 1.

18. The method of claim 17 wherein the compound is between 0.00000001 wt % and 20 wt % of the composition.

19. The method of claim 17 wherein the compound is between 0.0001 wt % and 10 wt % of the composition.

20. A method of treatment of vascular diseases and disorders comprising administering the compound of general formula (I), its stereoisomers, mixtures thereof and/or its cosmetically or pharmaceutically acceptable salts, according to claim 1, to contact a site of a mammal's body, the vascular disease or disorder being selected from the group consisting of aortic dissection, aneurysms, systolic arterial hypertension, and stroke.

* * * * *